(12) United States Patent
Sitkovsky et al.

(10) Patent No.: US 9,782,428 B2
(45) Date of Patent: Oct. 10, 2017

(54) METHOD FOR GENERATION OF BROADLY NEUTRALIZING ANTI-PATHOGEN ANTIBODIES

(71) Applicant: Northeastern University, Boston, MA (US)

(72) Inventors: Michail V. Sitkovsky, Boston, MA (US); Robert Koehler Abbott, Vienna, VA (US); Stephen Matthew Hatfield, Gonic, NH (US)

(73) Assignee: Northeastern University, Boston, MA (US)

(*) Notice: Subject to any disclaimer, the term of this patent is extended or adjusted under 35 U.S.C. 154(b) by 0 days.

(21) Appl. No.: 14/777,605

(22) PCT Filed: Mar. 18, 2014

(86) PCT No.: PCT/US2014/031104
§ 371 (c)(1),
(2) Date: Sep. 16, 2015

(87) PCT Pub. No.: WO2014/153363
PCT Pub. Date: Sep. 25, 2014

(65) Prior Publication Data
US 2016/0250248 A1    Sep. 1, 2016

Related U.S. Application Data

(60) Provisional application No. 61/803,066, filed on Mar. 18, 2013.

(51) Int. Cl.
| | | |
|---|---|---|
| *A61K 45/06* | (2006.01) | |
| *A61K 31/7076* | (2006.01) | |
| *A61K 39/39* | (2006.01) | |
| *C12N 5/0781* | (2010.01) | |
| *A61K 39/00* | (2006.01) | |

(52) U.S. Cl.
CPC .......... *A61K 31/7076* (2013.01); *A61K 39/39* (2013.01); *A61K 45/06* (2013.01); *C12N 5/0635* (2013.01); *A61K 2039/55511* (2013.01); *C12N 2501/05* (2013.01)

(58) Field of Classification Search
None
See application file for complete search history.

(56) References Cited

U.S. PATENT DOCUMENTS

| 8,080,554 B2 | 12/2011 | Sitkovsky et al. |
| 8,241,621 B2 | 8/2012 | Ichim |
| 2006/0093580 A1 | 5/2006 | Iwashima et al. |
| 2006/0292164 A1 | 12/2006 | Horwitz |
| 2010/0178299 A1 | 7/2010 | Sitkovsky et al. |
| 2011/0262442 A1* | 10/2011 | Hamilton ........... A61K 31/7076 424/139.1 |
| 2011/0300183 A1 | 12/2011 | Sitkovsky et al. |
| 2012/0093856 A1 | 4/2012 | Sitkovsky et al. |
| 2012/0202288 A1 | 8/2012 | Mendlein et al. |
| 2013/0014753 A1 | 1/2013 | Nezami |
| 2013/0101567 A1 | 4/2013 | Riley et al. |
| 2014/0377240 A1 | 12/2014 | Sitkovsky et al. |

FOREIGN PATENT DOCUMENTS

| WO | WO-00/29550 | 5/2000 |
| WO | WO-2007/040565 | 4/2007 |
| WO | WO 2011/126806 A1 | 10/2011 |

OTHER PUBLICATIONS

Fumero, et al. Immunosuppressive drugs as an adjuvant to HIV treatment. Journal of Antimicrobial Chemotherapy, vol. 53, No. 3, pp. 415-417, 2004.
International Search Report & Written Opinion on PCT/US2014/031104 dated Aug. 22, 2014.
Kang, et al. Cutting Edge: Immunosuppressant as Adjuvant for Tolerogenic Immunization. Journal of Immunology, vol. 180, No. 8, pp. 5172-5176 (2008).
Sitkovsky, et al. Hostile, Hypoxia-A2-Adenosinergic Tumor Biology as the Next Barrier to Overcome for Tumor Immunologists, Cancer Immunology Research, vol. 2, No. 7, pp. 598-605, Jul. 2014.
Notification of Transmittal of the International Preliminary Report on Patentability for Int'l Application No. PCT/US2014/031104, "Method for Generation of Broadly Neutralizing Anti-Pathogen Antibodies," date mailed, Oct. 1, 2015.
Notification of Transmittal of the International Preliminary Report on Patentability for Int'l Application No. PCT/US2013/021948, "Method and Compositions for Expanding Immunosupresive T Regulatory Cell in Vitro and Uses Thereof," date issued, Jul. 22, 2014; date mailed, Jul. 31, 2014.
Notification of Transmittal of the International Search Report and Written Opinion of the International Searching Authority for Int'l Application No. PCT/US2013/021948, "Method and Compositions for Expanding Immunosuppresive T Regulatory Cell in Vitro and Uses Thereof," date issued Mar. 19, 2013.
Hoffmann, Petra, et al., "Large-scale in vitro expansion of polyclonal human $CD4^+CD25^{high}$ regulatory T cells," Blood, vol. 104, No. 3, pp. 895-903, Aug. 2004.
Ernst, Peter B., et al., "Much Ado about Adenosine: Adenosine Synthesis and Function in Regulatory T Cell Biology," The Journal of Immunology, vol. 185, pp. 1993-1998, May 2010.
McCudden, C.R., et al., "G-protein signaling: back to the future," CMLS, vol. 62, pp. 551-577, Mar. 2005.
Mandapathil, Magis, et al., "Generation and Accumulation of Immunosuppressive Adenosine by Human $CD4^+CD25^{high}FOXP3^+$ Regulatory T Cells," The Journal of Biological Chemistry, vol. 285, No. 10, pp. 7176-7186, Mar. 5, 2010.
Kipnis, Jonathan, et al., "Dopamine, through the Extracellular Signal-Regulated Kinase Pathway, Downregulates $CD4^+CD25^+$ Regulatory T-Cell Activity: Implications for Neurodegeneration," The Journal of Neuroscience, vol. 24, No. 27, pp. 6133-6143, Jul. 7, 2004.

(Continued)

*Primary Examiner* — Brian J Gangle
(74) *Attorney, Agent, or Firm* — Hamilton, Brook, Smith & Reynolds, P.C.

(57) ABSTRACT

Methods and composition for potentiating germinal centers are disclosed herein. The methods include potentiating germinal centers to enhance antibody production in response to a vaccine, to increase antibody titer in response to a vaccine, and to enhance B cell class switching.

11 Claims, 49 Drawing Sheets

(56) References Cited

OTHER PUBLICATIONS

Bodor, Josef, et al., "Cyclic AMP underpins suppression by regulatory T cells," Eur J. Immunol, vol. 42, No. 6, pp. 1375-1384, Jun. 2012.
Peterson, Richard A., "Regulatory T-Cells: Diverse Phenotypes Integral to Immune Homeostasis and Suppression," Toxicologic Pathology, vol. 40, No. 2, pp. 186-204, Jan. 5, 2012.
Extended Supplementary European Search Report dated Apr. 30, 2015 in EP Application No. 13738627.2.
Extended Supplementary European Search Report dated Sep. 28, 2015 in EP Application No. 13738627.2.
Sitkovsky, M.V., et al., "Physiological Control of Immune Response and Inflammatory Tissue Damage by Hypoxia-Inducible Factors and Adenosine $A_{2A}$ Receptors," Annual Review of Immunology, Annual Reviews Inc., US, vol. 22, pp. 657-682, Apr. 1, 2004.
Sitkovsky, M.V., "T regulatory cells: hypoxia-adenosinergic suppression and re-direction of the immune response," Trends in Immunology, Elsevier Ltd., Trends Journals GB., vol. 30, No. 3, pp. 102-108, Mar. 1, 2009.
Choukèr, Alexander, et al., "Critical Role of Hypoxia and A2A Adenosine Receptors in Liver Tissue-Protecting Physiological Anti-Inflammatory Pathway," Molecular Medicine, vol. 14, No. 3-4, pp. 116-123, Jan. 1, 2008.
Ben-Shoshan, et al., "Hypoxia Controls CD4+CD25+ Regulatory T-Cell Homeostasis via Hypoxia-Inducible Factor-1α," Eur. J. Immunol., vol. 38, No. 9, pp. 2412-2418, Sep. 2008.
Clambey, et al., "Hypoxia-Inducible Factor-1 Alpha-Dependent Induction of FoxP3 Drives Regulatory T-Cell Abundance and Function During Inflammatory Hypoxia of the Mucosa," PNAS, vol. 109, No. 41, pp. E2784-E2793, Sep. 2012.
Riley, et al., "Human T Regulatory Cells as Therapeutic Agents: Take a Billion or So of These and Call Me in the Morning," Immunity, vol. 30, No. 5, pp. 656-665, May 2009.
Mahic, et al., "Differentiation of Naive CD4+ T Cells Into CD4+CD25+FOXP3+ Regulatory T Cells by Continuous Antigen Stimulation," Journal of Leukocyte Biology, vol. 83, pp. 1111-1117, May 2008.
Zheng, et al., "IL-2 is Essential for TGF-β to Convert Naive CD4+CD25-Cells to CD25+Foxp3+ Regulatory T Cells and for Expansion of These Cells," The Journal of Immunology, vol. 178, No. 4, pp. 2018-2027, Feb. 15, 2007.
Boomer, et al., "An Enigmatic Tail of CD28 Signaling," Cold Spring Harbor Perspectives in Biology, vol. 2, No. 8, 22 pages, Jun. 9, 2010.
Carswell, et al., "Low Oxygen Tension Enhances the Stimulation and Proliferation of Human T Lymphocytes in the Presence of IL-2," Cytotherapy, vol. 2, No. 1, pp. 25-37, Jan. 1, 2000.
Godfrey, et al., "In Vitro-Expanded Human CD4+CD25+ T-Regulatory Cells Can Markedly Inhibit Allogeneic Dendritic Cell-Stimulated MLR Cultures," Blood, American Society of Hematology, vol. 104, No. 2, pp. 453-461, Jul. 15, 2004.
Chen, et al., "$A^{2A}$ Adenosine Receptor Deficiency Attenuates Brain Injury Induced by Transient Focal Ischemia in Mice," Journal of Neuroscience, vol. 19, No. 21, pp. 9192-9200, Nov. 1, 1999.
Belikoff, et al., "A2B Adenosine Receptor Blockade Enhances Macrophage-Mediated Bacterial Phagocytosis and Improves Polymicrobial Sepsis Survival in Mice," Journal of Immunology, vol. 186, No. 4, pp. 2444-2453, Feb. 15, 2011.
Eltzschig, et al., "Purinergic Signaling During Inflammation," N. Engl. J. Med., vol. 367, No. 24, pp. 2322-2333, Dec. 13, 2012.
Kawano, Y., et al., "Low Telomerase Activity in $CD4^+$Regulatory T Cells in Patients With Severe Chronic GVHD After Hematopoietic Stem Cell Transplantation," Blood, vol. 118, No. 18, pp. 5021-5030, Nov. 2011.

* cited by examiner

B220-Blue

GL-7

A2bR-Red

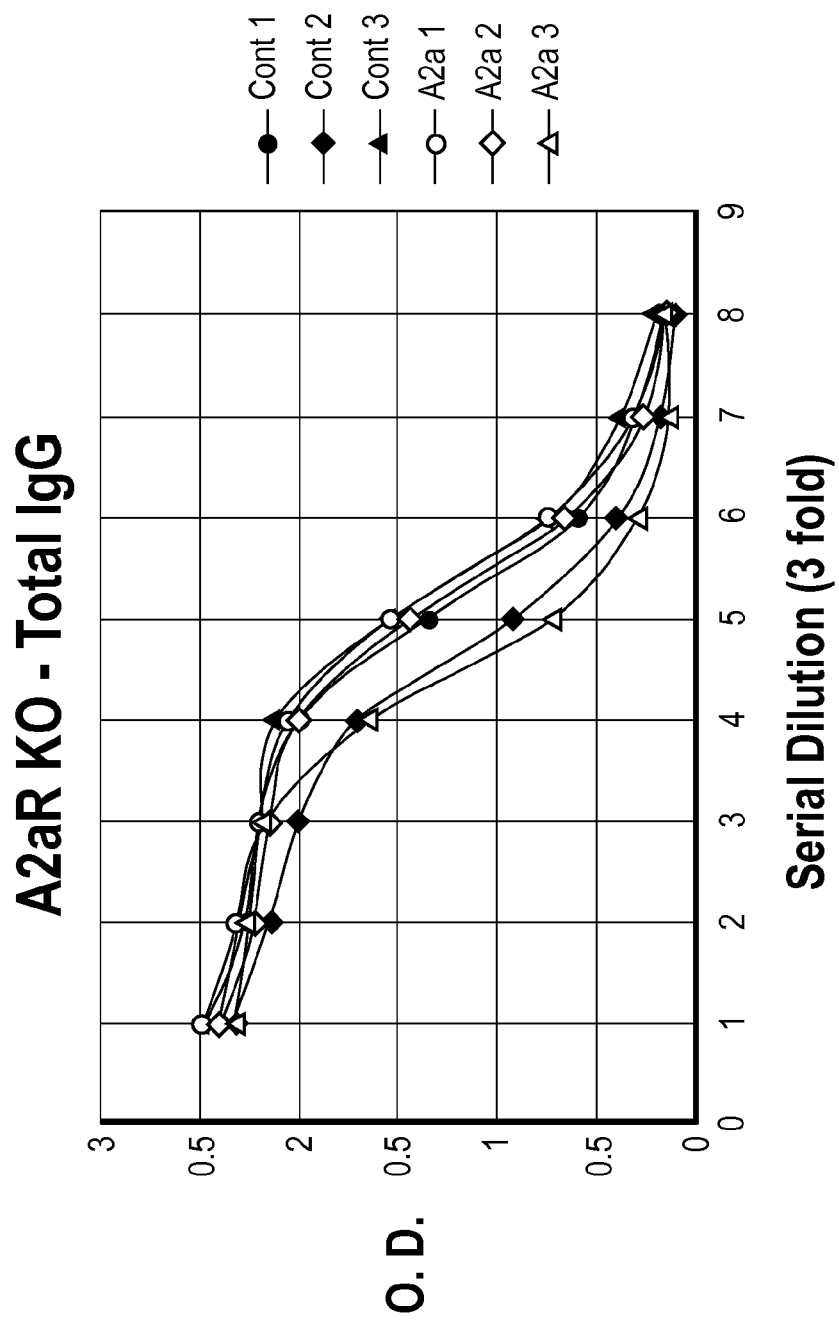

METHOD FOR GENERATION OF BROADLY NEUTRALIZING ANTI-PATHOGEN ANTIBODIES

CROSS-REFERENCE TO RELATED APPLICATIONS

This application is a U.S. National Stage of International Application No. PCT/US2014/031104, with international filing date Mar. 18, 2014, which claims the benefit of and priority to U.S. Provisional Application No. 61/803,066 filed Mar. 18, 2013, the contents of which are incorporated herein by reference in their entireties.

BACKGROUND

Broadly-neutralizing antibodies are cross-reactive antibodies that can bind to and neutralize multiple pathogens, such as multiple strains of a virus, e.g., influenza and HIV. For example, researchers have identified broadly-neutralizing HIV antibodies from a subject that was able to prevent 70% of 162 divergent HIV strains from establishing an infection.

SUMMARY

Disclosed herein are methods and compositions for enhancing an immune response in a subject. In some aspects, the method includes administering, after vaccination of the subject, one or more immune enhancers. In some embodiments, the immune enhancer includes one or more of an A2a adenosine receptor agonist; an A2b adenosine receptor agonist; a hypoxia inducible factor; and an agent that prevents the degradation of hypoxia inducible factors. In some embodiments, enhancing an immune response includes enhancing the production of high affinity antibodies. Additionally or alternatively, in some embodiments, enhancing an immune response includes enhancing the production of broadly neutralizing antibodies. Additionally or alternatively, in some embodiments, enhancing an immune response includes enhancing the rate of antibody production and/or increasing the quantity of antibody production.

In some embodiments, the method includes administering one or more additional immune enhancers. In some embodiments, the additional immune enhancers include one or more of Gi protein antagonists, an inhibitor of enzymes that degrade adenosine, an agent that activates adenylyl cyclase, an agent that increase the accumulation and/or production of extracellular adenosine, and agents that enhance the intracellular effects of A2a/A2b adenosine receptors or other Gs protein coupled receptors.

In some embodiments, the A2a adenosine receptor agonist is one or more of CGS21680, ATL146e, YT-146, Regadenozone, UK42,097. Additionally or alternatively, in some embodiments, the A2b adenosine receptor agonist is one or more of BAY 60-6583, LUF-5835, LUF-5845, N-ethylcarboxyamidoadenosine. Additionally or alternatively, in some embodiments, the hypoxia inducible factors is one or more of cobalt chloride (CoCl2), phenantrhonine, and prednisone In some embodiments, the method includes administering a vaccine prior to administration of the immune enhancer. In some embodiments, an adjuvant is administered simultaneously with the vaccine. In some embodiments, the adjuvant is one or more of aluminum salts, toll like receptor agonists and emulsions.

In some embodiments, the agent that enhances the intracellular effects of A2a/A2b adenosine receptors or other Gs protein coupled receptors is one or more of ibudilast, mesembrine, rolipram, piclamilast, luteolin, drotaverine and roflumilast.

In some embodiments, the one or more one immune enhancer is administered about 3 to 10 days after vaccination. In some embodiments, the one or more one immune enhancer is administered daily for about 3 to 42 days after vaccination.

In some embodiments, administration of the immune enhancer increases the NIP 5/NIP 25 ratio above 0.3.

In some aspects, a method for enhancing an antibody titer in response to vaccination is provided. In some embodiments, the method includes administering, after vaccination of the subject, one or more immune enhancers. In some embodiments, the immune enhancer includes one or more of Gs protein coupled receptor antagonists, Gi protein coupled receptor agonists, an agent that inhibits the effects of tissue hypoxia; an agent that inhibits the hypoxia inducible factor pathway, an agent that inhibits the accumulation of extracellular adenosine, and a treatment that inhibit the hypoxia inducible factor pathway.

In some embodiments, the Gs protein coupled receptor antagonist is one or more of dopamine, beta adrenergic, vasoactive intestinal peptide. In some embodiments, the Gi protein coupled receptor agonist is one or more of indomethacin, PGE2-EP3, sulprostone, MB28767, misoprostol, SC46275, and ONO-AE-249. In some embodiments, the treatment that inhibits the hypoxia inducible factor pathway includes inspiration of hyperoxic gas mixture or hyperbaric oxygen therapy. In some embodiments, the agent that inhibits the accumulation of extracellular adenosine is one or more of quercetin, APCP, α,β-Methylene adenosine 5'-diphosphate (AMP-CP), and POM-1.

In some aspects, a method for stimulating B cells, ex vivo is provided. In some embodiments, the method is useful to improve one or more of class switching, somatic mutation, and activation. In some embodiments, the method includes stimulating B cells in culture with antibodies, interleukins, and/or growth factors; and contacting the cells with an immune enhancer. In some embodiments, the immune enhancer is an A2a receptor agonist and/or an A2b receptor. In some embodiments, the cells are contacted with the immune enhancer under hypoxic conditions.

In some embodiments, the method further comprises contacting the cells with one or more additional immune enhancers. In some embodiments, the additional immune enhancer includes one or more of inhibitors of enzymes that degrade adenosine, an agent that activate adenylyl cyclase, an agent that increase the accumulation and/or production of extracellular adenosine, and an agent that potentiates or enhances the intracellular effects of A2a/A2b adenosine receptors or other Gs protein coupled receptors. In some embodiments, the A2a receptor agonist is one or more of CGS21680, ATL146e, YT-146, Regadenozone, UK42,097. In some embodiments, the A2a receptor agonist is one or more of CGS21680, ATL146e, YT-146, Regadenozone, and UK42,097. In some embodiments, hypoxic conditions include an oxygen concentration less than 21% or a condition wherein the partial pressure of oxygen is less than 159 mm/hg.

In some embodiments, the agent that potentiates or enhances the intracellular effects of A2a/A2b adenosine receptors or other Gs protein coupled receptors includes one or more of ibudilast, mesembrine, rolipram, piclamilast, luteolin, drotaverine, roflumilast.

In some embodiments, a method for potentiating a germinal center and/or cells within the germinal center of a subject is provided. In some embodiments, the method includes administering, after vaccination of the subject, one or more immune enhancers. In some embodiments, the immune enhancer is one or more of an A2a adenosine receptor agonist, an A2b adenosine receptor agonist, a hypoxia inducible factor, and an agent that prevents the degradation of hypoxia inducible factors.

In some embodiments, potentiating the germinal center and/or cells within the germinal center induces the development of high affinity antibodies. In some embodiments, potentiating the germinal center and/or cells within the germinal center induces the development of broadly neutralizing antibodies. In some embodiments, potentiating the germinal center and/or cells within the germinal center induces the development of high affinity broadly neutralizing antibodies. In some embodiments, potentiating the germinal center and/or cells within the germinal center comprises one or more of inducing a hypoxic environment and stimulating A2a and/or A2b adenosine receptors.

In some embodiments, the method further includes administering one or more additional immune enhancers. In some embodiments, the additional immune enhancer is one or more of: Gi protein antagonists, an inhibitor of enzymes that degrade adenosine, an agent that activates adenylyl cyclase, an agent that increase the accumulation and/or production of extracellular adenosine, and an agent that enhances the intracellular effects of A2a/A2b adenosine receptors or other Gs protein coupled receptors.

In some embodiments, the A2a receptor agonist is one or more of CGS21680, ATL146e, YT-146, Regadenozone, UK42,097. In some embodiments, the A2b receptor agonist is one or more of BAY 60-6583, LUF-5835, LUF-5845, N-ethylcarboxyamidoadenosine.

In some embodiments, the hypoxia inducible factor is one or more of cobalt chloride ($CoCl_2$), phenantrhonine, and prednisone.

In some embodiments, the agent that potentiates or enhances the intracellular effects of A2a/A2b adenosine receptors or other Gs protein coupled receptors is one or more of ibudilast, mesembrine, rolipram, piclamilast, luteolin, drotaverine, roflumilast.

In some embodiments, the one or more one immune enhancer is administered about 3 to 10 days after vaccination. In some embodiments, the one or more one immune enhancer is administered daily for about 3 to 42 days after vaccination.

BRIEF DESCRIPTION OF THE DRAWINGS

FIG. 7C total serum IgG from WT C57B/6 mice and A2a adenosine receptor knockout was assessed for total serum IgG as described. Knockout mice depicted as red lines, WT as Blue lines. Serial 3 fold dilutions on the x axis, optical density is on the y axis.

DETAILED DESCRIPTION

Figure 1A:
FIG. 1A is a slide showing hypoxic staining of mouse spleen immunized with NP-OVA/Alum 12 days post immunization.

The various concepts introduced above and discussed in greater detail below may be implemented in any of numerous ways, as the described concepts are not limited to any particular manner of implementation. Examples of specific implementations and applications are provided primarily for illustrative purposes.

As used here, the singular forms "a," "an" and "the" include plural referents unless the content clearly dictates otherwise. For example, reference to "a cell" includes a combination of two or more cells, and the like.

As used herein, the "administration" of an agent, vaccine, adjuvant, drug, or compound to a subject includes any route of introducing or delivering to a subject the agent, vaccine, adjuvant, drug, or compound to perform its intended function. Administration can be carried out by any suitable route, including, but not limited too orally, intranasally, parenterally (intravenously, intramuscularly, intraperitoneally, or subcutaneously), or topically. Administration includes self-administration and the administration by another.

As used herein, the term "agonist" refers to an agent that has affinity for and stimulates physiologic activity of a receptor normally stimulated by one or more naturally occurring agents, thus triggering a biochemical response. By way of example, but not by way of limitation, in some embodiments, an agonist is an agent that binds to an adenosine receptor, e.g., the A2a and/or A2b adenosine receptor, and activates the receptor and/or results in receptor activity or response.

As used herein, the term "antagonist" refers to an agent that interferes with or inhibits the physiological action of a chemical substance. For example, a receptor antagonist is an agent that reduces or eliminates the response that a ligand produces e.g., when the receptor antagonist is bound to the receptor and prevents, inhibits or modulates ligand access to the receptor. By way of example, but not by way of limitation, an antagonist may bind a receptor thereby inhibiting, preventing or reducing a biological response.

As used herein, the term "effective amount" or "therapeutically effective amount" refers to a quantity sufficient to achieve a desired effect, e.g., an amount of a compound which enhances an immune response to vaccination by developing high affinity, broadly neutralizing antibodies at higher quantities. By way of example, but not by way of limitation, in some embodiments, a therapeutically effective amount of an adenosine receptor agonist is the amount of adenosine receptor agonist necessary to potentiate or enhance the germinal center to develop high affinity, broadly neutralizing antibodies at higher quantities. In the context of antigenic applications, in some embodiments, the amount of a drug, agent, or compound administered to the subject will depend on the type of vaccine and/or adjuvant being given to the subject and on the characteristics of the individual, such as general health, age, sex, body weight and tolerance to drugs. The skilled artisan will be able to determine appropriate dosages depending on these and other factors.

As used herein, the term "enhanced immune response" refers to increasing the ability of a germinal center to generate specific types of antibodies, e.g., high affinity, broadly neutralizing antibodies, and/or generating antibodies at a higher rate.

As used herein, the term "immune enhancers" refers to agents that enhance or potentiate the germinal center and/or cell types in the germinal center for enhanced antibody production after administration of a vaccine. By way of example, but not by limitation, in some embodiments, enhanced antibody production includes, but is not limited to, increased production of high affinity antibodies, broadly neutralizing antibodies, or both, increased antibody titer, and/or enhancement of B cell class switching. By way of example, but not by way of limitation, in some embodiments, immune enhancers include agents which provide, stimulate or act to maintain an adenosine-rich and/or hypoxic environment. By way of example, but not by way of limitation, immune enhancers include A2a adenosine receptor agonists, A2b adenosine receptor agonists, hypoxia inducible factors, agents that prevents the degradation of hypoxia inducible factors, Gi protein antagonists, inhibitors of enzymes that degrade adenosine, agents that activate adenylyl cyclase, agents that increase the accumulation and/or production of extracellular adenosine, and agents that enhance or potentiate the intracellular effects of A2a/A2b adenosine receptors or other Gs protein coupled receptors.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

General

The germinal center is the site in which activated B cells undergo class switch recombination and somatic hypermutation in response to T dependent antigens in the weeks that follow antigenic stimulation. During the time following antigenic stimulation, the specific antibody that is produced increases its affinity for antigen in a gradual and stepwise manner, termed affinity maturation. Affinity maturation involves two interrelated processes:

1. Somatic hypermutation (SHM): During SHM, mutations are generated in the variable, antigen-binding coding sequences (known as complementarity-determining regions (CDR)) of the immunoglobulin genes. The mutation rate is up to 1,000,000 times higher than in cell lines outside the lymphoid system. The increased mutation rate result in 1-2 mutations per CDR and cell generation. The mutations alter the binding specificity and binding affinities of the resultant antibodies.

2. Clonal selection: B cells that have undergone SHM must compete for limiting growth resources, including the availability of antigen. The follicular dendritic cells (FDCs) of the germinal centers present antigen to the B cells, and only the B cell progeny with the highest affinities for antigen are selected to survive. Over several rounds of selection, the resultant secreted antibodies produced will have effectively increased affinities for antigen.

The A2a and A2b adenosine receptors, members of the Gs protein coupled receptors family, have been shown to play a role in both innate and cellular mediated adaptive immunity, but little is known of the roles of these receptors in B cell differentiation and antibody production. During innate and cellular mediated immunity excessive tissue damage leads to the development of hypoxic and extracellular adenosine rich microenvironments, which in turn suppress local inflammation via induction of cyclic AMP through Gs protein coupled A2a and A2b adenosine receptors. The generation of extracellular adenosine is mediated principally by ectoenzymes, such as CD73, which hydrolyzes adenosine monophosphate into adenosine.

Activation of the A2a and A2b adenosine receptors is generally known to have anti-inflammatory effects and activation of A2a and A2b adenosine receptors is known to be immunosuppressive. For example, Sitkovsky et al. (U.S. Pat. No. 8,080,554) disclose using A2a and A2b adenosine receptors antagonists to inhibit the activity of A2a and A2b adenosine receptors, as a method to increase an immune response.

Counter to teachings known in the art, in some embodiments, the present technology uses A2a and A2b adenosine receptor agonists to stimulate activity of A2a and A2b adenosine receptors, to enhance an immune response.

Potentiating the Germinal Center and/or Cells within the Germinal Center for an Enhanced Immune Response to Vaccination In some embodiments, the present technology relates to methods for enhancing an immune response to vaccination by potentiating the germinal center and/or the cells within the germinal center to produce high affinity, broadly neutralizing, serum antibodies. In some embodiments, the antibodies are produced faster and at higher quantities. For example in some embodiments, antibodies are produced faster and at higher quantities, e.g., as compared to an untreated subject.

In some embodiments, the germinal center and/or the cells within the germinal center are potentiated by stimulating receptors in the germinal center and/or in the cells within the germinal center. Cells within the germinal center include, but are not limited to, T-follicular helper cells, T-follicular regulatory cells, B cells, and FDCs, tingible body macrophages, stromal cells, and CD8 T regulatory cells. Targeted receptors include, but are not limited to, Gs protein coupled receptors and A2a and A2b adenosine receptors.

In some embodiments, the germinal center and/or the cells within the germinal center are potentiated by stimulating Gs protein coupled receptors. Additionally, or alternatively, in some embodiments, the germinal center and/or the cells within the germinal center are potentiated by stimulating A2a and/or A2b adenosine receptors. In some embodiments, the A2a and/or A2b adenosine receptors are stimulated through A2a and/or A2b receptors agonists. A2a receptor agonists include, but are not limited to, CGS21680, ATL146e, YT-146, Regadenozone, UK42,097. A2b receptor agonists include, but are not limited to, BAY 60-6583, LUF-5835, LUF-5845, N-ethylcarboxyamidoadenosine.

In some embodiments, the germinal center and/or the cells within the germinal center are potentiated by enhancing the intracellular effects of Gs protein coupled receptors, A2a/A2b adenosine receptors, or a combination thereof. In some embodiments, the intracellular effects of Gs protein coupled receptors and/or A2a/A2b adenosine receptors are enhanced by one or more agents, which include, but are not limited to, ibudilast, mesembrine, rolipram, piclamilast, luteolin, drotaverine, roflumilast.

In some embodiments, the germinal center and/or the cells within the germinal center are potentiated by inhibiting one or more Gi protein coupled receptors. In some embodiments, Gi protein coupled receptors are inhibited by using Gi protein receptor antagonists. Gi protein coupled receptors include, but are limited to, A1R and A3R.

In some embodiments, the germinal center and/or the cells within the germinal center are potentiated by providing one or more inhibitors of enzymes that degrade endogenous adenosine. Inhibitors that prevent the degradation of endogenous adenosine include, but are not limited to pentastatin and cladribine. By way of example, but not by limitation, in some embodiments, the enzyme that is inhibited from degrading endogenous adenosine is adenosine deaminase.

In some embodiments, the germinal center and/or the cells within the germinal center are potentiated by providing one or more agents that either directly or indirectly increase the accumulation and/or production of extracellular adenosine. In some embodiments, the agents that either directly or indirectly increase the accumulation and/or production of extracellular adenosine include inhibitors of the re-uptake/degradation pathway of extracellular adenosine. By way of example, but not by limitation, in some embodiments, equilibrative nucleoside transporters (ENTs) are inhibited to prevent the re-uptake/degradation of extracellular adenosine. Inhibitors of ENTs include, but is not limited to, dipyridamole.

In some embodiments, the germinal center and/or the cells within the germinal center are potentiated by providing one or more agents that either directly or indirectly activate adenylyl cyclase. Agents that directly stimulate adenylyl cyclase include, but are not limited to, forskolin.

In some embodiments, the germinal center and/or the cells within the germinal center are potentiated by combining one or more of the above discussed methods. By way of example, but not by way of limitation, in some embodiments, the germinal center and/or the cells within the germinal center are potentiated by administration of one or more of (i) A2a and/or A2b adenosine receptor agonists, e.g., CGS21680 and LUF-5835, (ii) an agent that enhances the intracellular effects of Gs protein coupled receptors, e.g., ibudilast, (iii) an agent that either directly or indirectly increases the accumulation and/or production of extracellular adenosine, (iv) inhibitors of enzymes that degrade endogenous adenosine, and (v) an agent that either directly or indirectly activates adenylyl cyclase.

Additionally or alternatively, in some embodiments, enhancing an immune response to vaccination includes inducing conditions within the germinal center microenvironment conducive for the production of antibodies, e.g., high affinity, broadly neutralizing antibodies. In some embodiments, the germinal center microenvironment is induced to be hypoxic. In some embodiments, a hypoxic germinal center microenvironment is induced by administering at least one agent that either directly or indirectly activates hypoxia inducible factors. Agents that either directly or indirectly activate hypoxia inducible factors include, but are not limited to, cobalt chloride ($CoCl_2$), phenantrhonine, and prednisone. In some embodiments, a hypoxic germinal center microenvironment is induced by administering at least one agent that either directly or indirectly prevents the degradation hypoxia inducible factors.

Methods for Inducing the Development of High Affinity, Broadly Neutralizing Antibodies In some embodiments, a method for inducing the development of high affinity, broadly neutralizing antibodies includes administration of a vaccine and one or more immune enhancers. In some embodiments, an adjuvant is administered with the vaccine.

Immune enhancers include, but are not limited to agents that potentiate the germinal center and/or the cells within the germinal center and one or more agents for inducing a hypoxic germinal center microenvironment.

Adjuvants include, but are not limited to, aluminum salts (e.g., ALHYDROGEL®), toll like receptor agonists (e.g., monophosphoryl lipid A (MPLA)), emulsions (e.g., MF-59), AS04, or combination thereof.

In some embodiments, the agent for potentiating the germinal center and/or the cells within the germinal center is a Gs protein coupled receptor agonist. Additionally, or alternatively, in some embodiments, the agent for potentiating the germinal center and/or the cells within the germinal center is an A2a and/or A2b adenosine receptor agonist. A2a receptor agonists include, but are not limited to, CGS21680, ATL146e, YT-146, Regadenozone, UK42,097. A2b receptor agonists include, but are not limited to, BAY 60-6583, LUF-5835, LUF-5845, N-ethylcarboxyamidoadenosine.

In some embodiments, the agent for potentiating the germinal center and/or the cells within the germinal center is an agent that enhances the intracellular effects of Gs protein coupled receptors, A2a/A2b adenosine receptors, or a combination thereof. In some embodiments, the agent that enhances the intracellular effects of Gs protein coupled receptors and/or A2a/A2b adenosine receptors includes, but is not limited to, ibudilast, mesembrine, rolipram, piclamilast, luteolin, drotaverine, roflumilast.

In some embodiments, the agent for potentiating the germinal center and/or the cells within the germinal center is a Gi protein coupled receptor antagonist. Gi protein coupled receptors include, but are limited to, A1R and A3R.

In some embodiments, the agent for potentiating the germinal center and/or the cells within the germinal center is an inhibitor of enzymes that degrade endogenous adenosine. Inhibitors that prevent the degradation of endogenous adenosine include, but are not limited to pentastatin and cladribine. By way of example, but not by limitation, in some embodiments, the enzyme that is inhibited from degrading endogenous adenosine is adenosine deaminase.

In some embodiments, the agent for potentiating the germinal center and/or the cells within the germinal center is an agent that either directly or indirectly increases the accumulation and/or production of extracellular adenosine. In some embodiments, the agents that either directly or indirectly increase the accumulation and/or production of extracellular adenosine include inhibitors of the re-uptake/degradation pathway of extracellular adenosine. By way of example, but not by limitation, in some embodiments, equilibrative nucleoside transporters (ENTs) are inhibited to prevent the re-uptake/degradation of extracellular adenosine. Inhibitors of ENTs include, but is not limited to, dipyridamole.

In some embodiments, the agent for potentiating the germinal center and/or the cells within the germinal center is an agent that either directly or indirectly activates adenylyl cyclase. Agents that directly stimulate adenylyl cyclase include, but are not limited to, forskolin.

In some embodiments, the agent for inducing a hypoxic germinal center microenvironment is an agent that either directly or indirectly activates hypoxia inducible factors. In some embodiments, a hypoxic germinal center microenvironment is induced by administering at least one agent that either directly or indirectly activates hypoxia inducible factors. Agents that either directly or indirectly activate hypoxia inducible factors include, but are not limited to, cobalt chloride ($CoCl_2$), phenantrhonine, and prednisone. In some embodiments, a hypoxic germinal center microenvironment is induced by administering at least one agent that either directly or indirectly prevents the degradation hypoxia inducible factors.

By way of example, but not by way of limitation, in some embodiments, a method for inducing the development of high affinity, broadly neutralizing antibodies includes administration of a vaccine, ALHYDROGEL®, an A2a receptor agonist (e.g., CGS21680), an A2b receptor agonist (e.g., BAY 60-6583), and an agent that induces hypoxia inducible factors.

In some embodiments, the vaccine, the one or more agents for potentiating the germinal center and/or the cells within the germinal center, and one or more agents for inducing a hypoxic germinal center microenvironment (i.e., collective called immune enhancers) are administered simultaneously. In some embodiments, an adjuvant is also administered simultaneously.

In another embodiment, the agents for potentiating the germinal center and/or the cells within the germinal center, and the agents for inducing a hypoxic germinal center microenvironment (i.e., collective called immune enhancers) are administered after administration of a vaccine or vaccine plus adjuvant. In some embodiments, the one or more agents for potentiating the germinal center and/or the cells within the germinal center and agents for inducing a hypoxic germinal center microenvironment are administered about 1 to 42 days, or about 2 to 35 day, or about 3 to 25 days, or about 4 to 20 days, or about 5 to 15 days, or about 6 to 10 days after administration of a vaccine or a vaccine plus adjuvant.

Alternatively, in some embodiments, the one or more agents for potentiating the germinal center and/or the cells within the germinal center and agents for inducing a hypoxic germinal center microenvironment (i.e., collective called immune enhancers) are administered daily for about 3 to 42 days, 2 to 35 days, or about 3 to 30 days, or about 4 to 25 day, or about 5 to 20 days, or about 6 to 15 days after administration of a vaccine or a vaccine plus adjuvant.

In some embodiments, enhanced (compared to untreated subjects) production of high affinity, broadly neutralizing antibodies is measured by a NIP-5/25 ratio approaching 1.0. In some embodiment, an NIP-5/25 ratio greater than about 0.3 is indicative of high affinity, broadly neutralizing antibody production. In some embodiments, an increase in NIP-5 is indicative of an increase of high affinity, broadly neutralizing antibodies. In some embodiments, the NIP-5/25 ratio increase is indicative of an increase in high affinity, broadly neutralizing antibodies.

Methods for Increasing the Titer of a Vaccination Response

In some embodiments, the present technology relates to methods for increasing the antibody titer in response to vaccination.

In some embodiments, the antibody titer in response to vaccination is increased by administering to a subject one or more of the following agents or treatments: (i) an agonist of Gi protein coupled receptors, (ii) agents that inhibits effects of tissue hypoxia, (iii) agents or treatments that inhibit the hypoxia inducible factor pathway, (iv) agents that inhibit the accumulation of extracellular adenosine. In some embodiments, the agent or treatment is administered after the administration of a vaccine or vaccine plus adjuvant.

In some embodiments, Gi protein coupled receptors include, but are not limited to, A1R and A3R. Agonists of Gi protein coupled receptors include, but are not limited to, and prostaglandin receptors. Prostaglandin receptors include, but are not limited to, PGD2 (e.g., indomethacin) and PGE2-EP3 (e.g., sulprostone, MB28767, misoprostol, SC46275, and ONO-AE-249).

Agents that inhibit effects of tissue hypoxia or inhibit the hypoxia inducible factor pathway include, but are not limited to, agents that increase oxygen carrying capacity of the blood (e.g., erythropoietin and darbepoietin).

Treatments that inhibit the hypoxia inducible factor pathway include, but are not limited to, inspiration of hyperoxic gas mixture, hyperbaric oxygen therapy, and any agent that inhibits hypoxia inducible factors. In some embodiments, a hyperoxic gas mixture is defined by a gas mixture with an oxygen concentration greater than the 21% atmospheric concentration of oxygen.

Agents or compounds that inhibit the accumulation of extracellular adenosine include, but are not limited to, inhibitors of enzymes involved in extracellular adenosine generation, inhibitors of transporters that either directly or indirectly supply metabolites, which can be broken down into adenosine, and inhibitors of any enzymes which directly or indirectly result in the accumulation of extracellular adenosine.

Inhibitors of enzymes involved in extracellular adenosine generation include, but are not limited to, inhibitors of CD39 or CD73. CD39 inhibitors include, but are not limited to, ARL 67156, POM-1, PSB 06126, and PSB 069. CD73 inhibitor include, but are not limited to, $\alpha,\beta$-Methyleneadenosine 5'-diphosphate sodium salt, and blocking antibody (Ty/11.8).

Inhibitors of transporters that either directly or indirectly supply metabolites, which can be broken down into adenosine include, but are not limited to, nitric oxide and insulin.

Enzymes that directly or indirectly result in the accumulation of extracellular adenosine include, but are not limited to, inhibitors of CD73 (e.g., quercetin), APCP, $\alpha,\beta$-Methylene adenosine 5'-diphosphate (AMP-CP), inhibitors of CD39 (e.g., POM-1).

In some embodiments, the agents are administered about 3 to 60 days, or about 5 to 55 days, or about 10 to 50 days, or about 15 to 45 days, or about 20 to 40 days, or about 25 to 35 days after vaccination. Alternatively, or additionally, in some embodiments, the agents are administered about 3 to 25 days, or about 5 to 20 days, or about 10 to 15 days after an immune boost or immune challenge. An immune boost or immune challenge are secondary vaccinations to improve antibody titer or antibody affinity. In some embodiments, immune boost or immune challenges include an adjuvant.

Methods for Improving Ex Vivo Class Switching of B Cells

In some embodiments, the present technology relates to methods for ex vivo stimulation of B cells to improve B cell class switching, somatic mutation, and/or overall activation.

In some embodiments, improving ex vivo B cell class switching, somatic mutation, and/or overall activation within the germinal center includes one or more of (i)

stimulation of B cells with antibodies (e.g., anti-IgM Fab2 and Anti-CD40), interleukins (e.g., IL-4), and/or growth factors and (ii) inducing a hypoxic germinal center microenvironment. In some embodiments, inducing a hypoxic germinal center microenvironment includes reducing the oxygen concentration (e.g., in cell culture) to less than atmospheric oxygen (which is typically about 21%) or reducing the partial pressure of oxygen in the culture to less than standard atmospheric oxygen pressure (which is about 159 mm/hg). Additionally, or alternatively, in some embodiments, inducing a hypoxic germinal center microenvironment includes treatment with agents that activate directly or indirectly hypoxia inducible factors, or prevent or inhibit the degradation of hypoxia inducible factors.

In some embodiments, improving ex vivo B cell class switching, somatic mutation, and/or overall activation includes stimulation B cells with antibodies (e.g., anti-IgM Fab2 and Anti-CD40), interleukins (e.g., IL-4), and/or growth factors and treatment with agents that directly or indirectly stimulate adenylyl cyclase. Agents that directly stimulate adenylyl cyclase include, but are not limited to, forskolin.

In some embodiments, improving ex vivo B cell class switching, somatic mutation, and/or overall activation includes stimulation B cells with antibodies (e.g., anti-IgM Fab2 and Anti-CD40), interleukins (e.g., IL-4), and/or growth factors and stimulating one or more A2a and/or A2b adenosine receptor. In some embodiments, the A2a and/or A2b adenosine receptors are stimulated through A2a and/or A2b receptors agonists. A2a receptor agonists include, but are not limited to, CGS21680, ATL146e, YT-146, Regadenozone, UK42,097. A2b receptor agonists include, but are not limited to, BAY 60-6583, LUF-5835, LUF-5845, N-ethylcarboxyamidoadenosine.

In some embodiments, improving ex vivo B cell class switching, somatic mutation, and/or overall activation within the germinal center includes stimulation with antibodies (e.g., anti-IgM Fab2 and Anti-CD40), interleukins (e.g., IL-4), and/or growth factors and treatment with agents that potentiates the intracellular effects of Gs protein coupled receptors, A2a/A2b adenosine receptors, or a combination thereof. In some embodiments, the agents that potentiates the intracellular effects of Gs protein coupled receptors and/or A2a/A2b adenosine receptors includes, but is not limited to, ibudilast, mesembrine, rolipram, piclamilast, luteolin, drotaverine, roflumilast.

Modes of Administration

Any method known to those in the art for administration of vaccines, drugs, agents, or compounds may be employed. Suitable methods include in vitro, ex vivo, or in vivo methods. In vivo methods typically include, e.g., the administration of a vaccine, an adjuvant, and one or more germinal center regulating agents or compounds, such as those described above, to a mammal, e.g., a human. When used in vivo for therapy, the germinal center regulating agents or compounds are administered to the subject in effective amounts (e.g., amounts that have desired antigenic effect). The dose and dosage regimen will depend upon factors such as but not limited to, the vaccination being given to the subject, the characteristics of the particular germinal center regulating drugs, agents, or compounds used, the subject, and the subject's history.

The effective amount may be determined during pre-clinical trials and clinical trials by methods familiar to physicians and clinicians. An effective amount of an agent useful in the methods may be administered to a mammal in need thereof by any of a number of well-known methods for administering pharmaceutical compounds. The vaccine, adjuvant, and one or more germinal center regulating drugs or compounds may be administered systemically or locally.

The germinal center regulating drugs or compounds are typically formulated to be compatible with its intended route of administration. Examples of routes of administration include, but are not limited to, parenteral (e.g., intravenous, intradermal, intraperitoneal or subcutaneous).

Sterile injectable solutions can be prepared by incorporating the active drug or compound in the required amount in an appropriate solvent, as required, followed by filtered sterilization. Generally, dispersions are prepared by incorporating the active compound into a sterile vehicle, which contains a basic dispersion medium and the required other ingredients.

Dosage, toxicity, and antigenic efficacy of the drugs or compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human. Additionally or alternatively, in some embodiments, birds (e.g., commercially valuable species such as chickens and turkeys, etc.) may be treated in accordance with the methods disclosed herein.

Pharmaceutical Compositions and Effective Dosages

In some embodiment, the drugs, agents, and compounds useful for potentiating germinal centers to enhance response to vaccination are in the form of a pharmaceutical composition.

In some embodiments, the pharmaceutical compositions includes at least one Gs protein coupled agonist, such as an A2a or A2b adenosine receptor agonist, and/or at least one hypoxia inducible factor and/or compounds that prevents the degradation of hypoxia inducible factors. In some embodiments, the pharmaceutical composition also includes one or more additional agents to potentiate the germinal center to enhance production of high affinity antibodies. Additional agents include, but are not limited to, Gi protein antagonists, inhibitors of enzymes that degrade adenosine, compounds that activate adenylyl cyclase, compounds that increase the accumulation and/or production of extracellular adenosine, and compounds that potentiate the intracellular effects of A2a/A2b adenosine receptors or other Gs protein coupled receptors.

In some embodiments, the Gs protein coupled receptor agonist is an A2a and/or A2b adenosine receptor agonist. A2a receptor agonists include, but are not limited to, CGS21680, ATL146e, YT-146, Regadenozone, UK42,097. A2b receptor agonists include, but are not limited to, BAY 60-6583, LUF-5835, LUF-5845, N-ethylcarboxyamidoadenosine.

In some embodiments, the factor or compound for inducing a hypoxic germinal center microenvironment is an agent that either directly or indirectly activates hypoxia inducible factors. Agents that either directly or indirectly activate hypoxia inducible factors include, but are not limited to, cobalt chloride (CoCl2), phenantrhonine, and prednisone. In some embodiments, a hypoxic germinal center microenvironment is induced by administering at least one agent that either directly or indirectly prevents the degradation hypoxia inducible factors.

In some embodiments, compounds that potentiates the intracellular effects of Gs protein coupled receptors and/or A2a/A2b adenosine receptors includes, but is not limited to, ibudilast, mesembrine, rolipram, piclamilast, luteolin, drotaverine, roflumilast.

In some embodiments, Gi protein coupled receptors include, but are not limited to, A1R and A3R.

In some embodiments, the compound for potentiating the germinal center and/or the cells within the germinal center is an inhibitor of enzymes that degrade endogenous adenosine. Inhibitors that prevent the degradation of endogenous adenosine include, but are not limited to pentastatin and cladribine. By way of example, but not by limitation, in some embodiments, the enzyme that is inhibited from degrading endogenous adenosine is adenosine deaminase.

In some embodiments, the agent for potentiating the germinal center and/or the cells within the germinal center is an agent that either directly or indirectly increases the accumulation and/or production of extracellular adenosine. In some embodiments, the agents that either directly or indirectly increase the accumulation and/or production of extracellular adenosine include inhibitors of the re-uptake/degradation pathway of extracellular adenosine. By way of example, but not by limitation, in some embodiments, equilibrative nucleoside transporters (ENTs) are inhibited to prevent the re-uptake/degradation of extracellular adenosine.

In some embodiments, the agent for potentiating the germinal center and/or the cells within the germinal center is an agent that either directly or indirectly activates adenylyl cyclase. Agents that directly stimulate adenylyl cyclase include, but are not limited to, forskolin.

In some embodiments, the pharmaceutical composition is formulated with an appropriate solid or liquid carrier, depending upon the particular mode of administration chosen. The pharmaceutically acceptable carriers and excipients useful in a pharmaceutical composition as those commonly use in the art. By way of example, but not by limitation, parenteral formulations usually comprise injectable fluids that are pharmaceutically and physiologically acceptable fluid vehicles such as water, physiological saline, other balanced salt solutions, aqueous dextrose, glycerol or the like. Excipients that can be used include, but are not limited to, other proteins, such as human serum albumin or plasma preparations.

In some embodiments, the pharmaceutical composition to be administered can also contain minor amounts of non-toxic auxiliary substances, such as wetting or emulsifying agents, preservatives, and pH buffering agents and the like, for example, sodium acetate or sorbitan monolaurate.

In some embodiments, other medicinal and pharmaceutical agents, for instance another immunostimulant, also can be included Immunostimulants include, but are not limited to, IFA, COX-2 inhibitors, IL-12, saponins (e.g., QS-23), and N-acetyl-cysteine.

In some embodiments, the dosage form of the pharmaceutical composition will be determined by the mode of administration chosen. By way of example, but not by limitation, in addition to injectable fluids, topical and oral formulations can be employed. Topical preparations can include eye drops, ointments, sprays and the like. Oral formulations can be liquid (e.g., syrups, solutions or suspensions), or solid (e.g., powders, pills, tablets, or capsules). In some embodiments, solid compositions, conventional non-toxic solid carriers can include pharmaceutical grades of mannitol, lactose, starch, or magnesium stearate. Actual methods of preparing such dosage forms are known, or will be apparent, to those skilled in the art.

In some embodiments, the pharmaceutical compositions are formulated in unit dosage form, suitable for individual administration of precise dosages. By way of example, and not by limitation, unit dosage can contain from about 1 mg to about 1 g of adenosine receptor agonist. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The pharmaceutical compounds can be administered to humans or other animals on whose cells they are effective in various manners such as topically, orally, intravenously, intramuscularly, intraperitoneally, intranasally, transdermally, intradermally, intrathecally, and subcutaneously. The particular mode of administration and the dosage regimen will be selected by the attending clinician, taking into account the particulars of the case (e.g., the subject, the disease, the disease state involved, and whether the treatment is prophylactic). Treatment can involve daily or multi-daily doses of compound(s) over a period of a few days to months, or even years.

In some embodiments, an effective amount of an adenosine receptor, e.g., A2a or A2b adenosine receptor, agonist administered in a single dose, or in several doses, for example daily, during a course of treatment. However, the effective amount of an adenosine receptor agonist is dependent on the specific agonist applied, the subject being treated, the severity and type of the affliction, and the manner of administration of the therapeutic(s). By way of example, but not by limitation, in some embodiments, a therapeutically effective amount of an adenosine receptor agonist can vary from about 0.01 mg/Kg body weight to about 1 g/Kg body weight.

EXAMPLES

The present examples are non-limiting implementations of the use of the present technology.

Example 1. Germinal Centers have a Hypoxic Microenvironment Post Immunization This example shows that germinal centers have a hypoxic microenvironment post immunization.

Materials and Methods

Immunization of Mice:

10-12 week old female C57B/6 mice (Charles River Laboratories, Wilmington, Mass.) were immunized with immunogen (4-hydroxy-3-nitrophenyl-acetyl-Ovalbumin, i.e., NP-OVA) and alum hydroxide (Aluminum Sulfate, EMD Cat#AX0735-1), which was prepared as a 10% solution v/v in PBS. The NP-OVA and alum hydroxide was mixed at an equal volume at a concentration of 0.01 mg/ml in sterile PBS (1 ml of 10% Alum hydroxide+1 ml of PBS/immunogen) in a 50 ml Falcon Conical. 1 molar KOH (prepared in milli-Q filtered Deionized water) was added in a dropwise manner until the pH reached 6.5. The solution was then washed with 30 ml of sterile PBS and centrifuged for 10 minutes at 2500 rpm at 4 degrees Celsius. The supernatant was aspirated and wash/centrifugation was repeated 2 more times. Before centrifugation, pellet was fully resuspended by vortexing. The final suspension was reconstituted to a total volume of 1.8 ml in sterile PBS for immunization of 9 mice (200 µl/mouse, 1 µg/mouse, assuming 10% loss of immunogen). Mice were immunized with a 1 ml syringe (25 gauge needle) via intraperitoneal injection.

Hypoxic conditions in the germinal center microenvironment resulting from immunization was measured by administration of HYPDXYPROBE® (Hypoxyprobe, Inc., Burlington, Mass.), to the immunized mice. HYPDXYPROBE® was dissolved at a concentration of 10 mg/ml in hanks balanced salt solution. The mice were injected with the of HYPDXYPROBE® preparation at a dose of 100 mg/kg intravenously through the tail vein.

After 12 days, the mice were sacrificed and their spleens or lymph nodes were harvested and embedded in OCT Tissue Tek compound and frozen by dipping in liquid nitrogen. 5 micrometer tissue sections were cut on a cryostat and mounted onto superfrost plus slides. Slides were dried at room temperature for one hour and fixed in 1:1 acetone methanol fixative for 10 minutes at −20 degrees. Slides were stored until further immunostaining at −20 degrees.

Staining:

Slides were warmed to room temperature for 15 minutes, then Pap pen was applied around tissue sections and dried for 15 minutes. Slides were rehydrated for 20 minutes in IHC buffer which consisted of 0.5% BSA/0.1% tween 20 in PBS. Fc Block (BD Biosciences, 2.4g2) was diluted 1:200 in IHC buffer and added to sections for 20 minutes prior to incubation with primary antibodies. Various primary antibodies were added at the same time for 3 hours. Antibodies consisted of GL-7 (clone GL-7; red) for the germinal center, B220 (RA3-6B2; blue) for the B cell follicle, and HYPDXYPROBE® (HP-1; green) for the HYPDXYPROBE® (FIG. 1A). A secondary antibody, ALEXA FLUOR® A488 (Invitrogen, Grand Island, N.Y.), was added separately at a concentration of 1:200 as an amplification step of HYPDXYPROBE®. All the antibodies above were diluted in IHC buffer. The dilution ratios were as follows: GL-7 1:200, B200 1:400, HYPDXYPROBE® 1:100, and ALEXA FLUOR® A488 1:200.

Flow Cytometry:

Germinal center B cells and T follicular helper cells were analyzed by flow cytometry for single cell analysis to confirm if they were hypoxic by HYPDXYPROBE® staining. Single cells suspensions of spleens and lymph nodes were generated by manual grinding using 3 ml sterile syringe in FACS buffer (5% FBS in PBS with 1× Penicillin/streptomycin). Germinal center B cells were gated on lymphocytes, B220+, FAS hi, G1-7 Hi, while non-germinal center B cells were gated on Lymphocytes, B220+, FAS negative, GL-7 negative. T follicular helper cells were gated on CD4 positive, ICOS positive, PD-1 positive, Non CD4 T cells were gated on lymphocytes, CD4 positive, ICOS negative, PD-1 negative.

Staining of Vasculature:

Immunized mice, as described above, where sacrifice at day 17 and subject to spleen harvesting and staining protocols discussed above. Vasculature was stained for using the CD31-phycoerythrine, which was diluted at 1:200 in IHC buffer.

Results

Figure 1B:
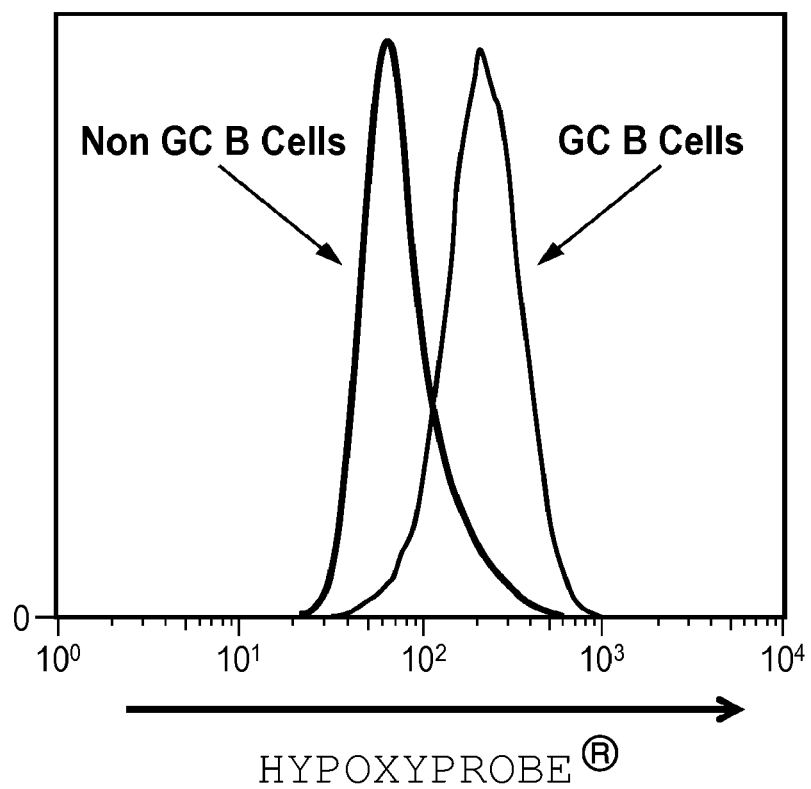
FIG. 1B is a graph showing that the germinal center B cells were hypoxic 12 days post immunization.
Figure 1C:
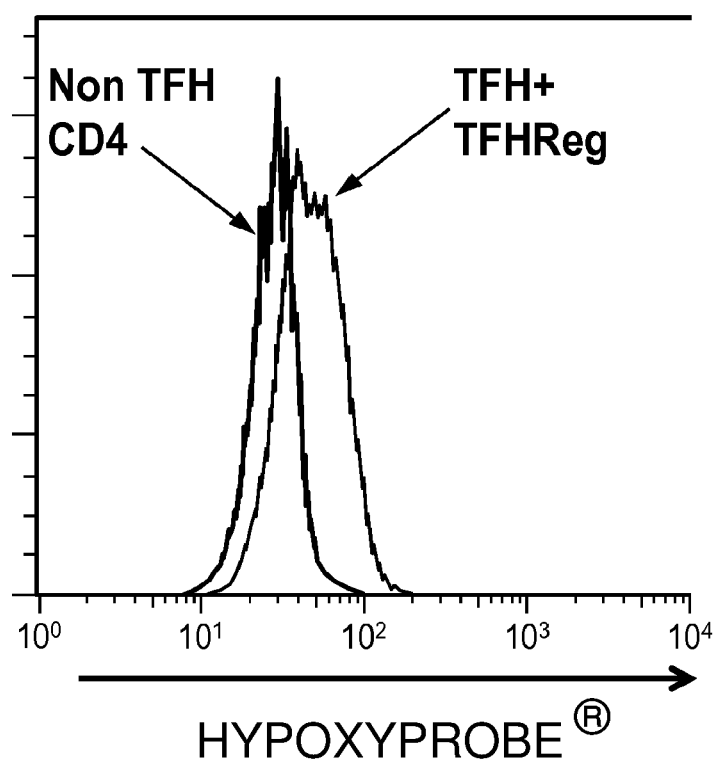
FIG. 1C is a graph showing that the T-Follicular helper cells were hypoxic 12 days post immunization.
Figure 1D:
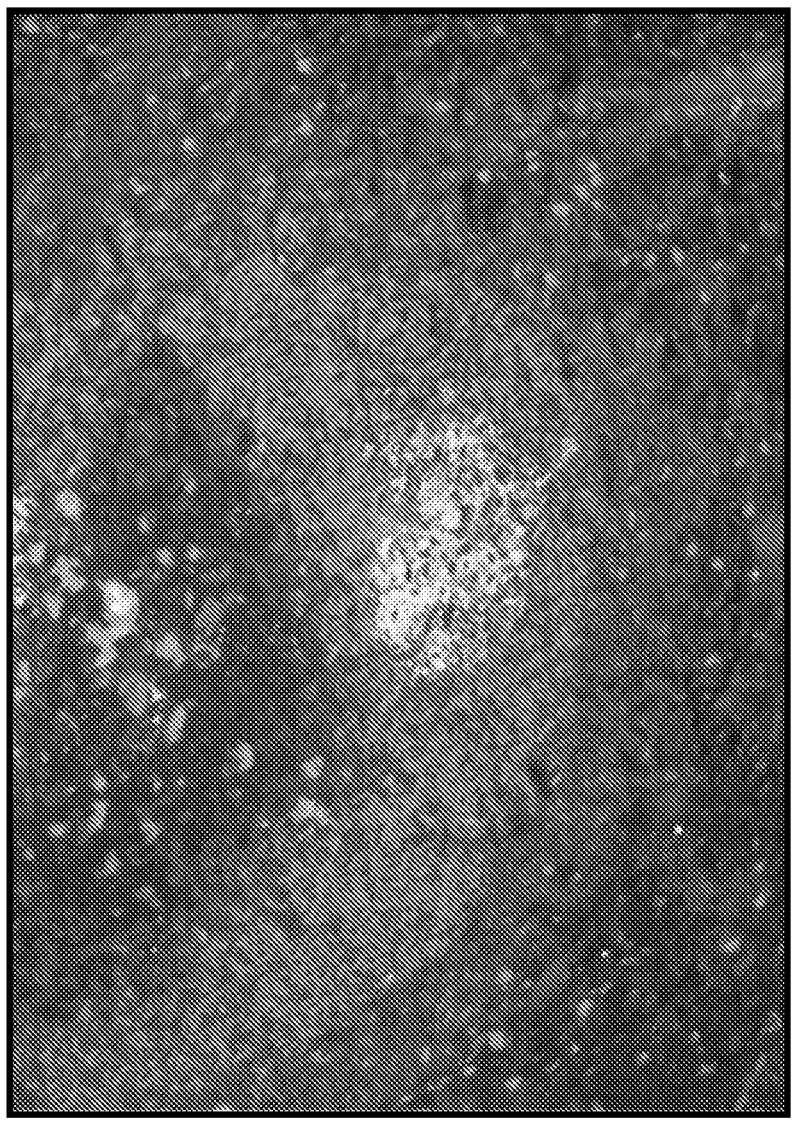
FIG. 1D is a slide showing vasculature staining with endothelial marker CD31 of a mouse spleen 17 days following immunization.
Figure 1E:
FIG. 1E is a slide showing vasculature staining with endothelial marker CD31 of a control B cell follicle without a germinal center.

The tissue histology showed that the injectable tracer HYPDXYPROBE®, which binds to proteins in under 1% oxygen tension, accumulates within splenic germinal centers 12 days post vaccination, the peak of the germinal center reaction (FIG. 1A). Analysis by flow cytometry confirmed that germinal center B cells and T follicular helper cells appear hypoxic as determined by level of HYPDXYPROBE® staining (FIG. 1B). Since tissue histology and flow cytometry confirmed that the germinal center was a low oxygen environment, the vasculature was stained using CD31 and it was observed that the germinal center is poorly vascularized when compared to control B cell follicle (FIG. 1C).

The results show that germinal centers have a hypoxic microenvironment in response to immunization. Accordingly, the results demonstrate that enhancing or maintaining the hypoxic microenvironment of the germinal centers is useful for enhancing the effects of vaccination.

Example 2. Germinal Centers have an Extracellular Adenosine Rich Microenvironment Post Immunization This example shows that germinal centers have an extracellular adenosine rich microenvironment post immunization.

Materials and Methods 25 mice were immunized as described in Example 1, and 5 mice were assessed at days 8, 12, 16, and 36 following immunization.

Figure 2A:
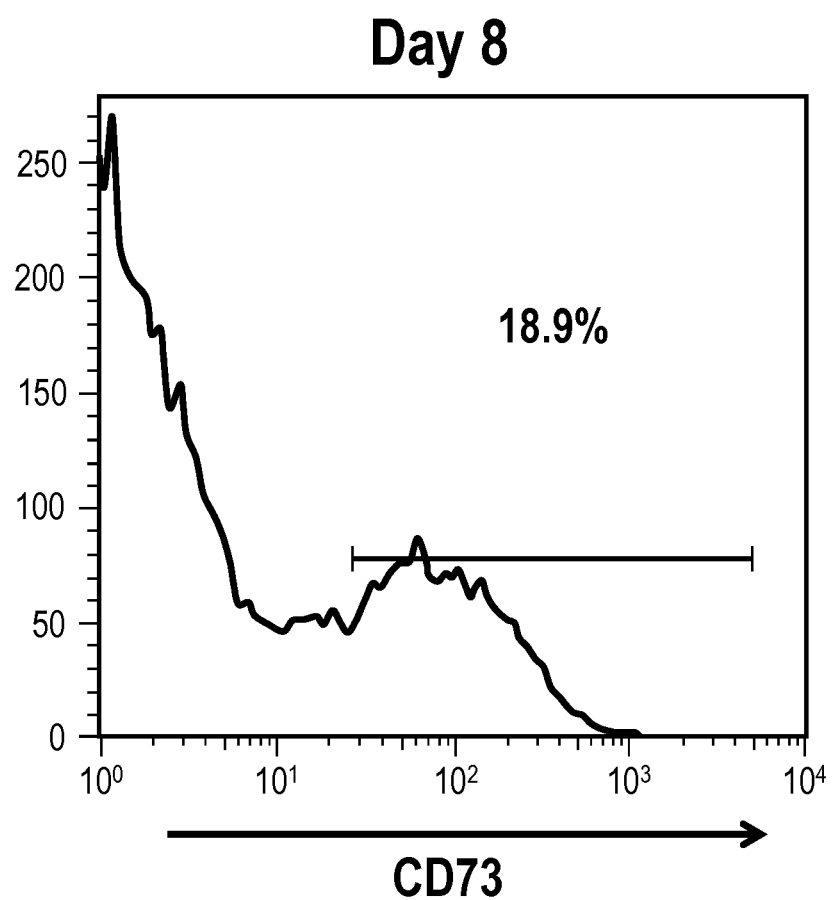
FIG. 2A is a graph showing flow cytometric analysis of germinal center B cells following immunization with NP-OVA/Alum at day 8.

The expression of extracellular adenosine generating enzyme CD73 was measured as a distinct marker of extracellular adenosine. Flow cytometric analysis of germinal center B cells for CD73 was assessed for mice at days 8, 12, 16, and 36 following immunization (FIG. 2A). Germinal center B cells were gated as lymphocytes, B220+, Fas+, GL-7+.

Mice sacrificed at day 12 following immunization were sacrificed and the spleens were fixed and stained for CD73 using CD73-Phycoerythrine, clone Ty/11.8 (eBioscience, San Diego, Calif.)(see FIG. 2B), which was diluted at 1:100-1:200 in IHC buffer, using the staining protocol in Example 1. Germinal center and B cell follicle staining are also the same as described in FIG. 1C.

Once flow cytometric analysis was completed on the BDFACSCalibur, the files were exported as FCS-1.0 files and analyzed on Flowjo software (Treestar, Eugene, Oreg.).

Figure 2B:
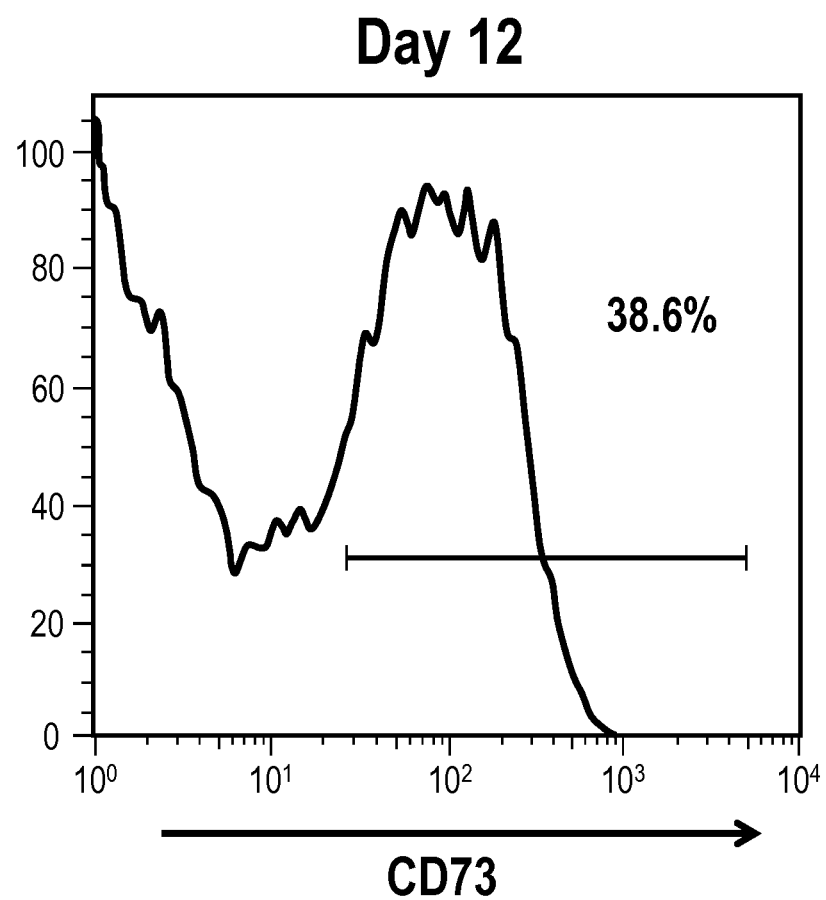
FIG. 2B is a graph showing flow cytometric analysis of germinal center B cells following immunization with NP-OVA/Alum at day 12.
Figure 2C:
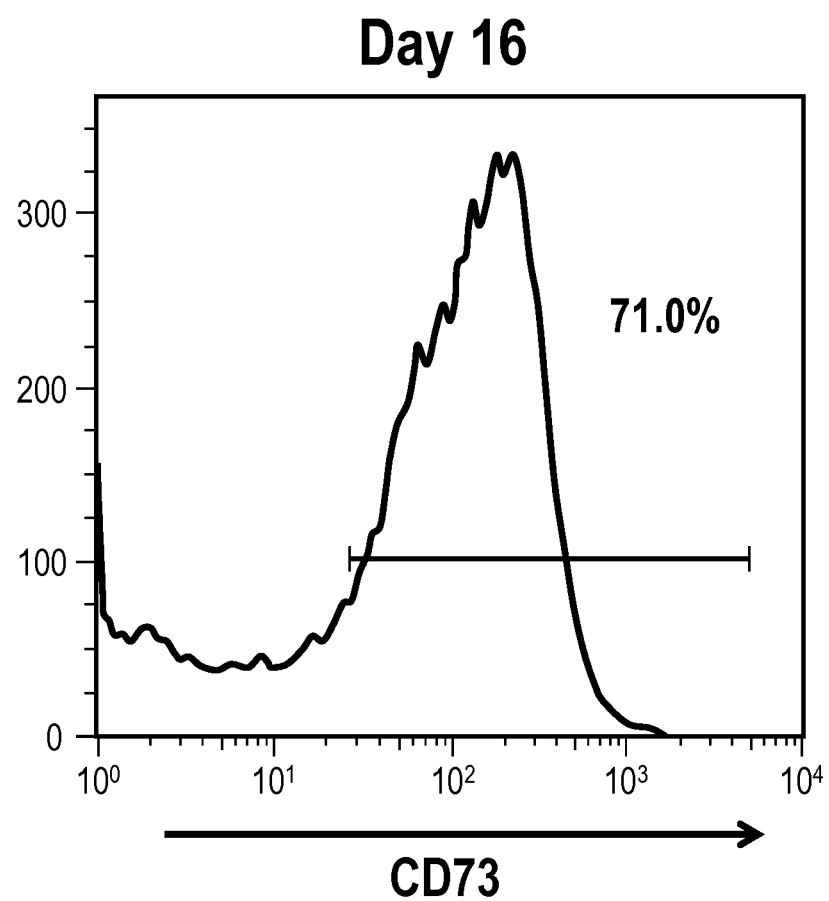
FIG. 2C is a graph showing flow cytometric analysis of germinal center B cells following immunization with NP-OVA/Alum at day 16.

Total mean fluorescence intensity was analyzed for gated for germinal center B cells with B220+, Fas+, Gl-7+ expression and the CD73 fluorescence was recorded for at days 8, 12, 16, and 36 following immunization (FIG. 2C).

Figure 2D:
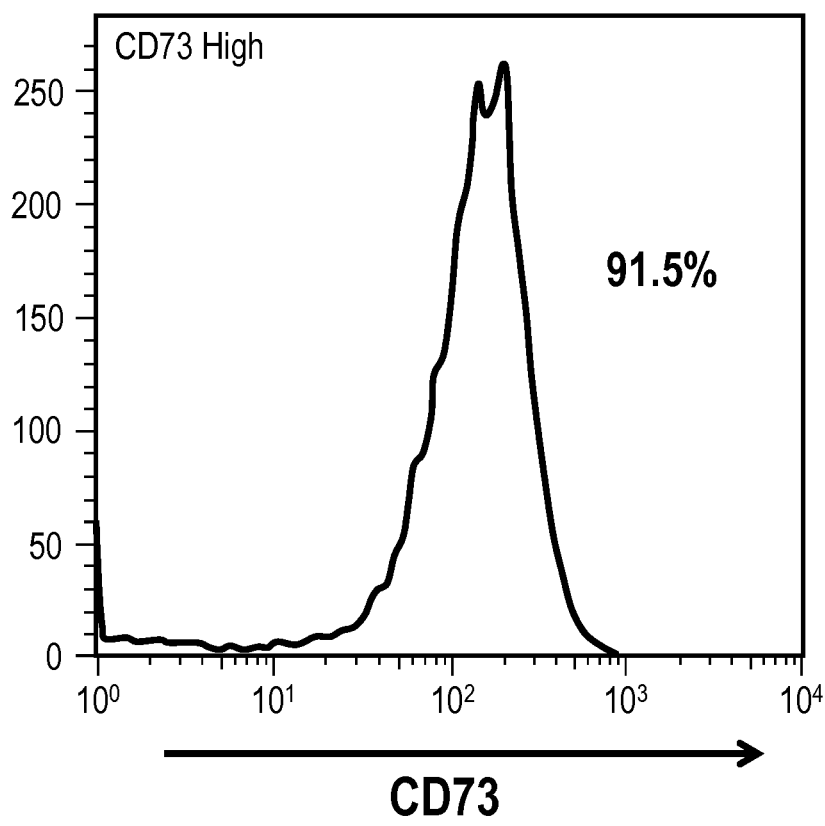
FIG. 2D is a graph showing flow cytometric analysis of germinal center B cells following immunization with NP-OVA/Alum at day 36.
Figure 2E:
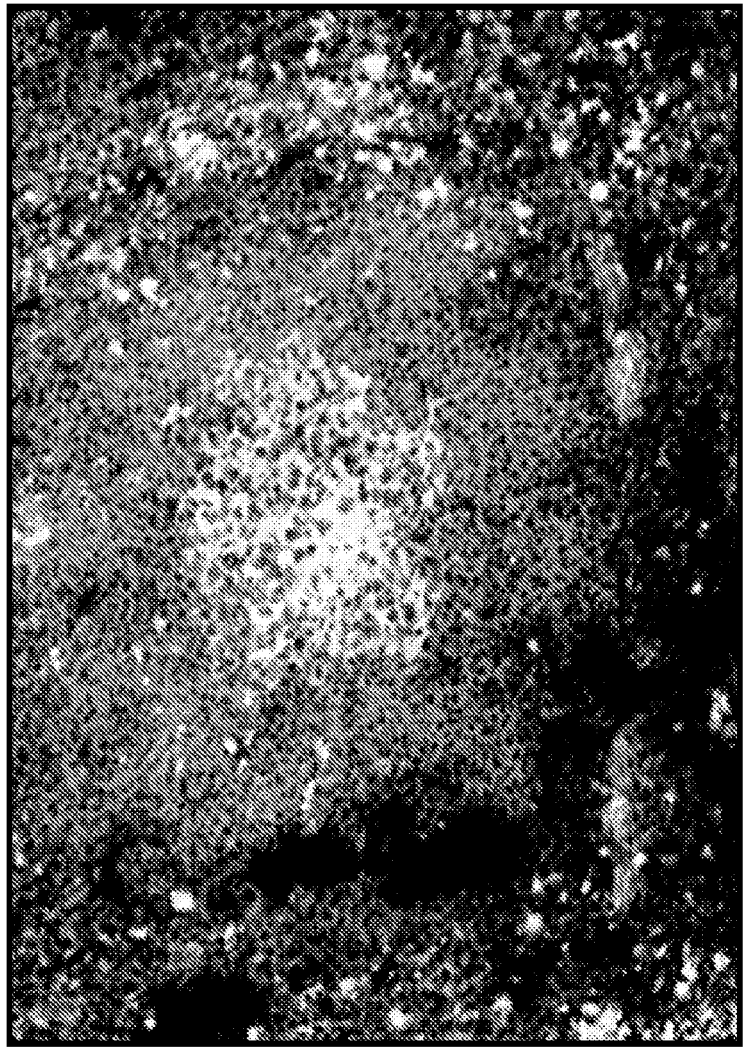
FIG. 2E is a slide showing the localization of CD73 within the germinal center in spleen of a mouse immunized with NP-OVA/Alum, 12 days post immunization.
Figure 2F:
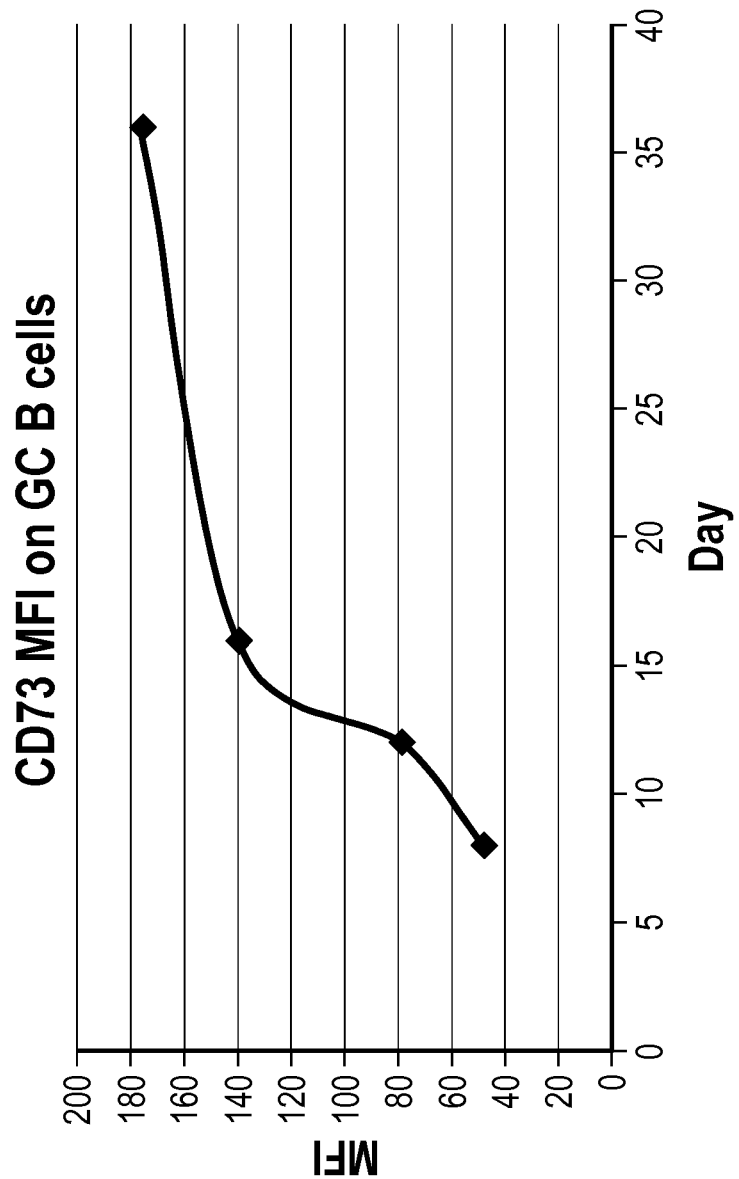
FIG. 2F is a graph showing that the total mean fluorescence intensity of CD73 expression on germinal center B cells increases over the course of immunization with NP-OVA/Alum.
Figure 2G:
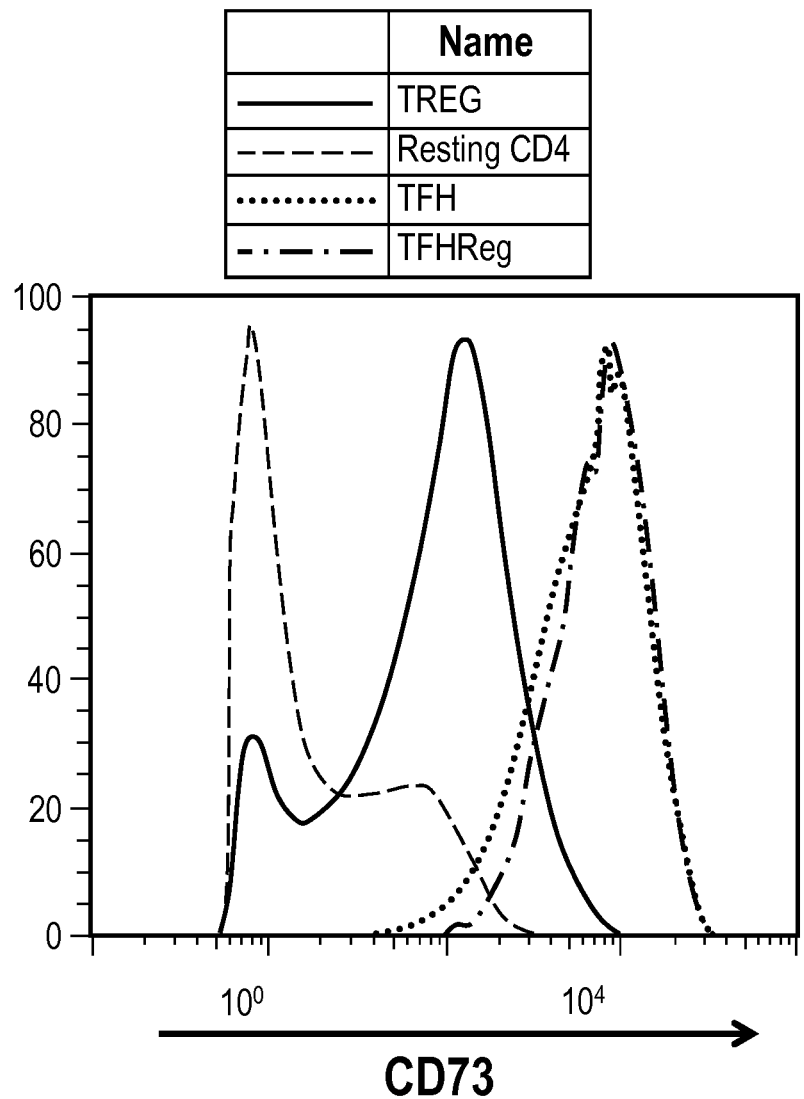
FIG. 2G is a graph showing expression of CD73 on various CD4 T cell subsets.

CD73 was assessed on CD4 T cells by flow cytometry (FIG. 2D). Flow cytometry was performed on a FACSAria I. CD4 T cells at different states were harvested from 10-12 week old female C57B/6 mice. Using the flow cytometry protocol of Example 1, T follicular helper and T follicular helper regulatory cells were defined as CD4 Positive, TCR-Beta Positive (clone H57-597, Biolegend), and triple defined ICOS high, PD-1 high, CXCR5 High (CXCR5 Biotin—eBioscience, clone SPRCL5, 1:100 dilution. Secondary antibody was added separately, Streptavidin-BV421 (Biolegend, 1:100). T follicular helper and T follicular helper regulatory cells were separated by FoxP3 staining.

Results

Flow cytometry showed a gradual increase in the expression of CD73 in germinal center B cells over the course of vaccination (FIG. 2A). The increase of CD73 correlated with a decrease in frequency of germinal center B cells (FIG. 2A). Tissue histology of mouse spleen 12 days following immunization with NP-OVA/Alum showed co-localization of CD73 within the germinal center (FIG. 2B). Total mean fluorescence intensity of CD73 expression on germinal center B cells increases over the course of immunization with NP-OVA/Alum (FIG. 2C). Additionally, it was observed that both T follicular helper and T follicular helper regulatory cells are among the highest expressers of CD73 in the spleen (FIG. 2D).

The results show germinal center have an extracellular enriched adenosine microenvironment. The results also show that the cell types in the germinal center utilize extracellular adenosine signaling within the germinal center. Accordingly, these results demonstrate that increasing extracellular adenosine in the germinal center microenvironment is useful for enhancing the effects of vaccination.

Example 3. Identifying Adenosine Receptors Expressed in the Germinal Center and in the Cell Types within the Germinal Center This example shows that the A2b adenosine receptors is expressed in the germinal center and in B cells, whereas the A2a adenosine receptors is expressed in T follicular helper and T follicular regulatory cells.

Materials and Methods

Single cells suspension of spleen and lymph node cells from immunized mice were sorted on FACSAria II (germinal center B cells gated on B220+, Fas+, Gl-7+, sorted at 70 PSI/70 micron nozzle). Germinal center cells were pelleted and snap frozen in liquid nitrogen. Cells were then stored at −20 C until further analysis.

Cells were re-suspended in 1 ml RNA-stat60 and standard RT-PCR for assessment of mouse A2aR and A2bR mRNA was performed using sybr-green. Expression level was normalized to Ig-Beta (CD79b). Non-germinal center B cells defined as B220+, Gl-7−, Fas−.

Mouse spleen tissue was fixed and stained according to protocol in Example 1. A2b adenosine receptor was identified with A2bR antibody AB1589P (Millipore, Billerica, Mass.) antibody (red) diluted at 1:100, B cell follicles were identified using B200+(blue), and germinal center was identified using GL-7 (green) as described in Example 1.

T-follicular helper cells/T-follicular regulatory cells and CD4 T cells (control) were derived from single cell suspensions of mouse spleen from mice immunized as described in Example 1 (i.e., 1 µg/mouse NP-OVA in precipitated Alum hydroxide). Cells were harvested day 8 following immunization Five mice spleens were combined and stained at the same time to acquire cells during sorting process.

T-follicular helper cells/T-follicular regulatory cells or CD4 T cell control were sorted by flow cytometry and incubated with various adenosine receptor agonists, e.g., A2a receptor agonist (CGS-21680, Tocris, Minneapolis, Minn.), A2b receptor agonist (Bay-60-6583, Tocris, Minneapolis, Minn.) or N-ethylcarboxyamidoadenosine (NECA) (a non-specific agonist, Tocris, Minneapolis, Minn.). Each agonist was added at a concentration of 10 mM of drug in a reaction volume of 50 µl of media. Cells per reaction tube were 20,000 of TFH/TFHReg cells or CD4 T cell control. Triplicate reaction vials were run for each condition. Media consisted of standard mouse serum 10% fetal bovine serum, 1× Penicillin/Streptamycin, 55 mM 2-Mercaptoethanol in IMDM (Iscove's Modified Dulbelco's Medium) (Gibco).

The cells were incubated in 37° C. water bath for 15 minutes and then lysed using HCl and total downstream induced cAMP was measured by ELISA kit protocol (using the non-acetylation protocol) from GE Healthcare titled "cAMP direct Biotrak EIA."

Results

Figure 3A:
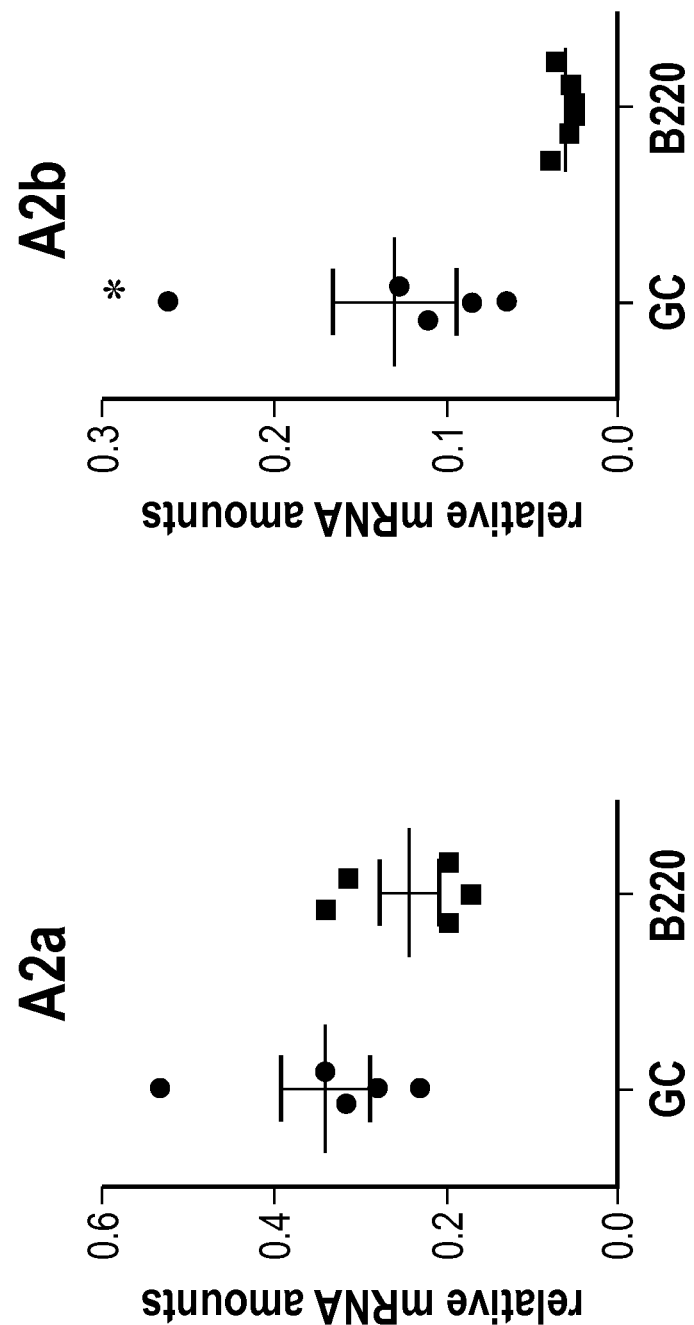
FIG. 3A are graphs showing RT-PCR analysis of A2a and A2b receptor expression levels on germinal center and non-germinal center B cells 10 days following immunization with NP-OVA/Alum.
Figure 3B:
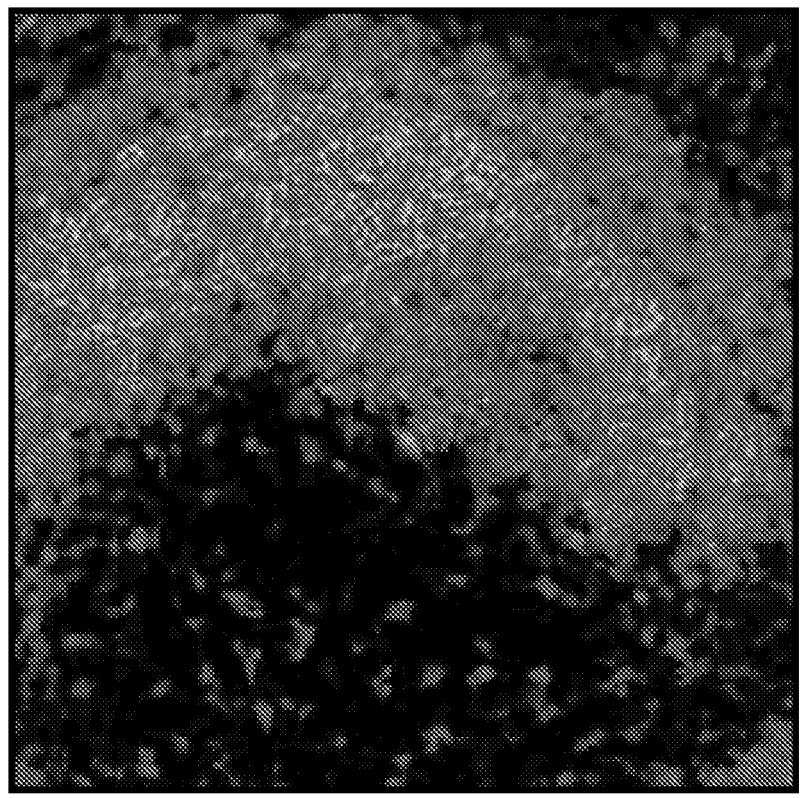
FIG. 3B is a slide showing localization of the follicle in spleen of an unimmunized mouse.
Figure 3C:
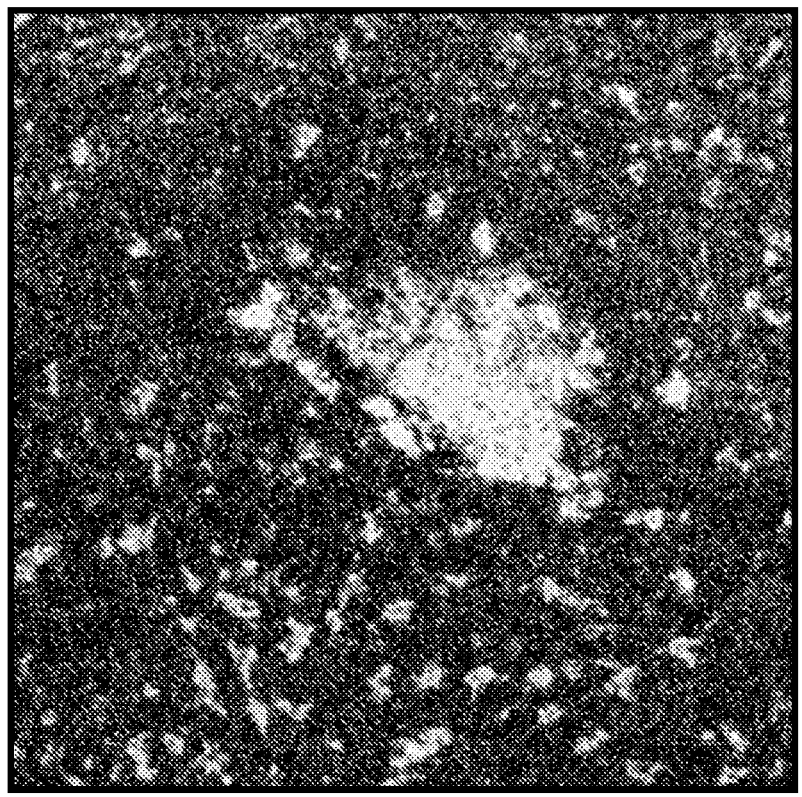
FIG. 3C is a slide showing localization of the germinal center in spleen of an unimmunized mouse.
Figure 3D:
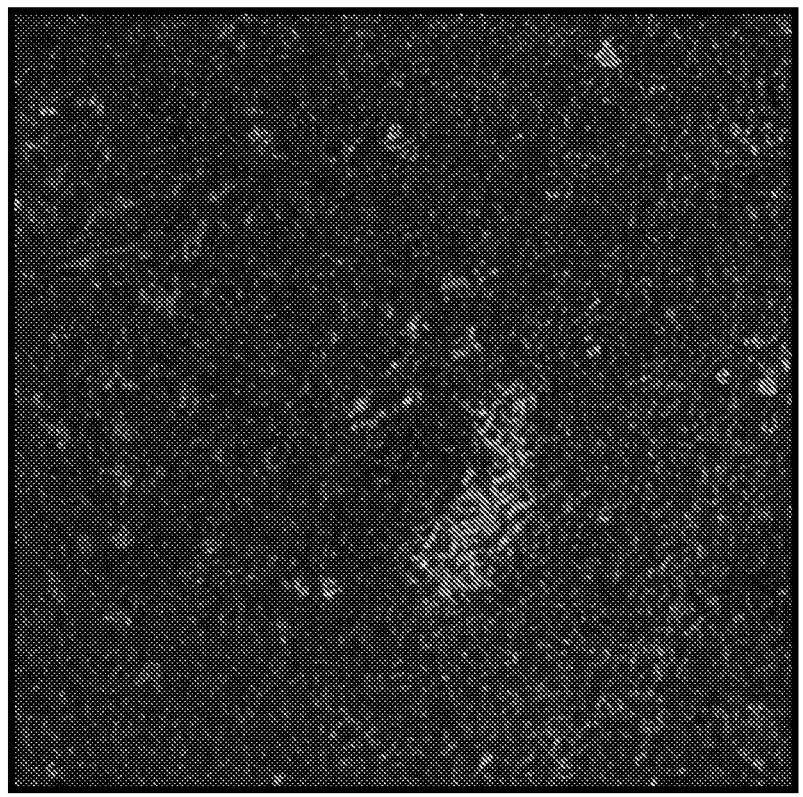
FIG. 3D is a slide showing localization of the A2b adenosine receptor in spleen of an unimmunized mouse.
Figure 3E:
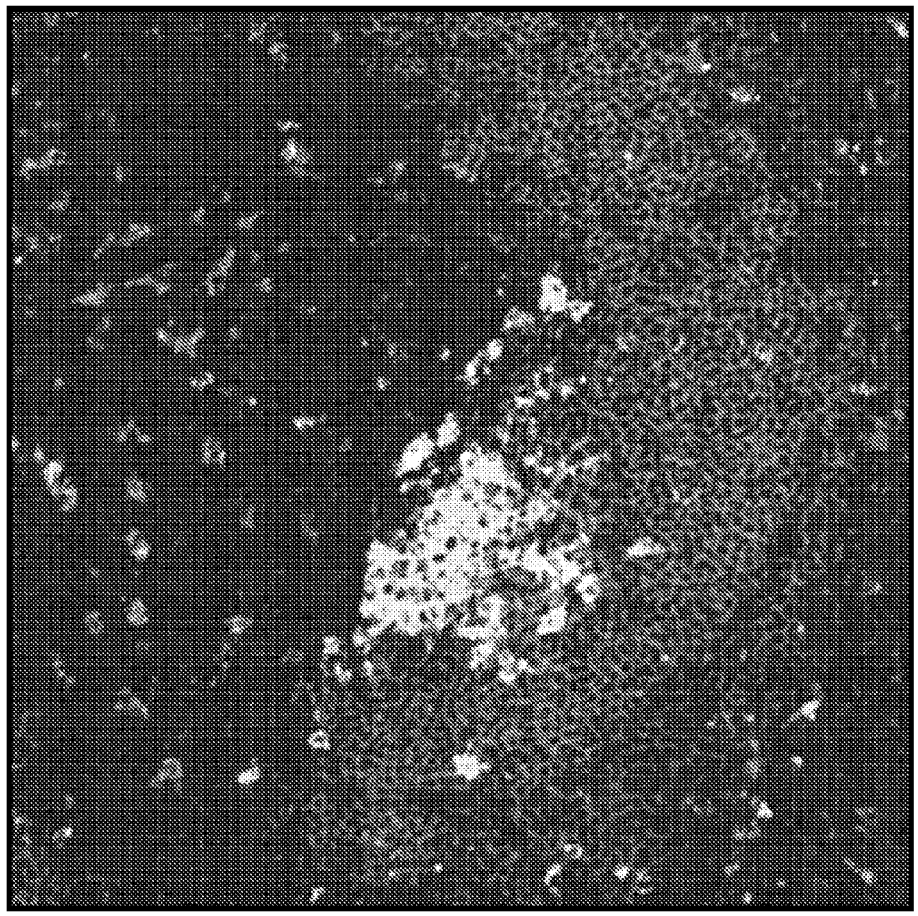
FIG. 3E is a slide showing localization of A2b receptor expression at the protein level within the germinal center in spleen of an unimmunized mouse, i.e., the merge of FIGS. 3B-3d.
Figure 3F:
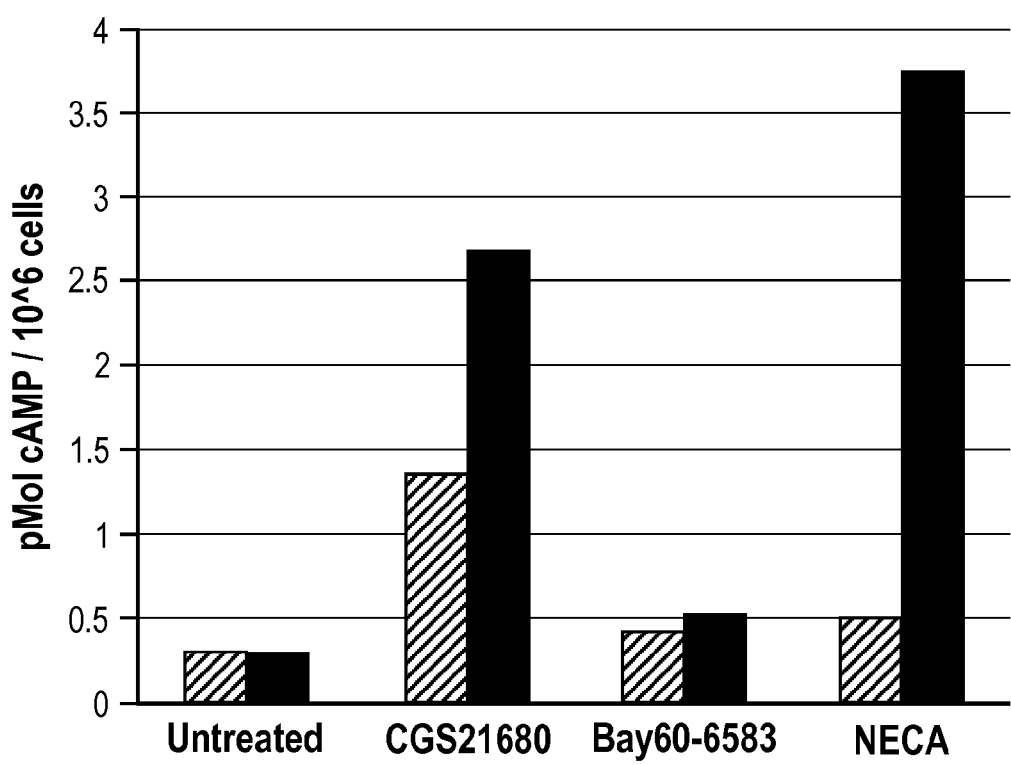
FIG. 3F is a graph showing functional expression level of A2a adenosine receptors on T follicular helper/T follicular helper regulatory cells (red bars) compared to CD4 T cell controls (blue bars).

Immunostaining showed that the A2b adenosine receptors are highly expressed within the light zone of the germinal center (FIG. 3B). Additionally, RT-PCR showed that the mRNA of A2b adenosine receptors is up regulated in sorted germinal center B cells (FIG. 3A). Functional A2b adenosine receptors were expressed on the protein level in T Follicular helper/T follicular regulatory cells as compare to control CD4 T cells (control) as measured by the increase in cAMP after stimulation of the A2b receptor with various adenosine receptor agonists (FIG. 3C).

These result show that functional A2b adenosine receptors are highly expressed in the germinal center. Accordingly, stimulating the A2b adenosine receptor is useful for enhancing an immunogenic response in the germinal centers.

Example 4. CD73 and the A2a/A2b Adenosine Receptors are Involved IgM to IgG Class Switching In Vivo This example shows that CD73 and A2a/A2b adenosine receptors play a role in class switching recombination.

Materials and Methods

Knockout mice that lacked A2a adenosine receptors, A2b adenosine receptors, or ecto-enzyme CD73 were assayed for levels of IgM, IgA, and IgG.

A2a adenosine receptor knockout mice were purchased/received from Dr. Jiang-Fan Chen. The A2a adenosine receptor knockout mice were generated according to the protocol described in Chen et al., *Journal of Neuroscience*, 19(21): 9192-9200 (Nov. 1, 1999).

The A2b adenosine receptor knockout mice were generated according to the protocol described in Belikoff et al., *Journal of Immunology*, 186(4): 2444-53 (Feb. 15, 2011).

CD73 knockout mice were purchased from the Jackson Labs (strain B6.129S1-Nt5etm1Lft/J). The originally strain was donated by Linda F. Thompson, Oklahoma Medical Research Foundation.

Serum Collection:

Serum from mice was obtained via retro-orbital eye bleed and serum was collected into serum separator tubes (BD).

Mouse serum quantitation kits for IgA, IgG, and IgM (Bethyl Labs, Montgomery, Tex.) were used in the ELISA assays to serum levels of IgA, IgG, and IgM. 50 µl of sample was used per well in 96-well plates. Starting dilution for mouse serum for total Ig was 1:1000 and serial 3 fold dilutions were used. Eight total 3 fold dilutions (i.e., top well 1:1000, second well 1:3000, and third well 1:9000) per mouse was used to assess the full binding range in the ELISA. Linear range of the curve of binding was used to assess relative amounts of serum Ig. All antibodies and serum were diluted in blocking buffer (0.5% BSA in 1×PBS). Wash Buffer consisted of (0.5% BSA in 1×PBS with 0.1% tween 20).

The role of A2a adenosine receptors in antibody generation and germinal center kinetics was assayed by immunization of A2a adenosine knockout mice and weekly tracking of affinity kinetics of total antigen specific (NIP-25) and high affinity antigen specific (NIP-5) antibody in serum by ELISA. The ratio of NIP-5/25 should approach 1, indicating that all of the antibody in the serum is high affinity antibody.

Ten knockout A2a adenosine receptor mice (i.e., 10A2aR KOs) were immunized with NP-OVA/Alum as described in Example 1. Ten age/sex matched C57B/6 mice WT (controls) (Charles River Labs, Wilmington, Mass.) were immunized with NP-OVA/Alum as described in Example 1.

Mice were harvested on day 64 and flow cytometric analysis was performed on spleen homogenates. Mice were bled once every week for serum (50 µl blood collected in capillary tube and 35 µl serum recovered from the BD serum separator tubes) starting at day 0 and going up to day 64. To assay affinity kinetics, the H331g1 antibody, which is a hybridoma produced by IgG that is specific for NP/NIP, was used to assess the quantity of high affinity antibodies. The H331g1 antibody was obtained from Dr. Garnett Kelsoe at Duke University. Starting dilution of the H331g1 was 0.732 mg/ml and it was further diluted to 1:500 for the top well of the ELISA. Serial 3 fold dilutions for 6 generations were used to quantify (i.e., 1:500, 1:1500, 1:4500). A total of 7 generations of standards were used in duplicate.

Flow Cytometric Staining Procedure:

Spleens from the above mice were harvested and manually mashed with end of 5 ml syringe, filtered through 70 micron nylon mesh filter (BD Biosciences) into a 50 ml Falcon tube using FACS Buffer (1×PBS, 5% FBS, 1× Penicllin/Streptomycin), and spun at 1500 RPM, 7 minutes. Supernatent was decanted, the pellet was re-suspended in 2 mL ACK Lysis buffer (Gibco) for 2 minutes, and then diluted with 10 mL FACS Buffer to stop the reaction. Suspension was filtered again through 70 micron strainer into new tube and spun again. Pellet was re-suspended in 5 mL FACS Buffer and counted using trypan blue (Gibco) (stock trypan blue solution diluted 1:5 using PBS) exclusion on a hemocytometer.

10 million cells were transferred to 1.2 mL cluster tubes for FACS Staining. Cells were pelleted (500×g for 5 minutes) and the supernatant aspirated leaving about 60 µl of buffer in the tube. Cells were vortexed and 20 µl of master mix FC block (BD Bioscience, clone 2.4G2) was added to each tube. Cells with master mix FC Block were incubated at 4° C. for 15 minutes.

After the 15 minute incubation, 20 µl of master mix antibodies was added directly to each FC blocked sample and incubated for 20 minutes at 4° C. By way of example, but not by limitation, in some embodiments, master mixes antibodies to identify germinal center B cells include: GL-7-Biotin (eBioscience, clone GL-7, 1:400, B220-APC (BD Bioscience, clone RA3-6B2); 1:200, CD38 FITC (BD Biosciences, clone 90), and 1:100, NP-PE (Biosearch Technologies). By way of example, but not by limitation, in some embodiments, master mix antibodies to identify T follicular helper/regulatory cells include: CD4 FITC (BD Biosciences, clone RM4-5, 1:200), PD-1 PE (eBiosciences, clone RMP1-30, 1:100), ICOS-Biotin (BD Biosciences, clone 17.7E9, 1:100).

The primary reagents of master mix antibodies were all mixed together and added at the same time. The cells were incubated with the master mix antibodies for 20 minutes at 4° C. After the 20 minutes they were washed off with 700 µl of FACS buffer and cells were pelleted and supernatant removed. After the wash, 80 µl of secondary reagent, streptavidin-PEcy7 (BD Biosciences, 1:400), was added for 20 minutes at 4° C.

The cells were then fixed and permeabilized using the FoxP3 Fixation Permeabilization kit (eBiosciences). FoxP3 antibody (eBiosciences, clone FJK-16S, 1:50) was diluted in permeabilzation buffer and added to cells for 1 hour at 4° C. After this, cells were washed twice with permeabilaztion buffer and run on a FACSCalibur (Beckton Dickenson) equipped with 4 parameters and two lasers (488 nm and 633 nm). Single color controls were used to set up compensation on the machine before each individual panel was run. All samples in FIGS. 7C-7D were run on this machine. Germinal center B cells were defined as B220+, Gl-7+, CD38−, and TFH Cells were defined as CD4+, PD-1high, ICOS high, while TFHRegs were defined as CD4+, PD-1high, ICOShigh, FoxP3+. Mean fluorescence intensity was determined by the level of fluorescence recorded of FOXp3 on T follicular helper/regulatory cells. Values were obtained in analysis software Flowjo from the gates as stated above (Treestar, Eugene, Oreg.).

Results

Figure 4A:
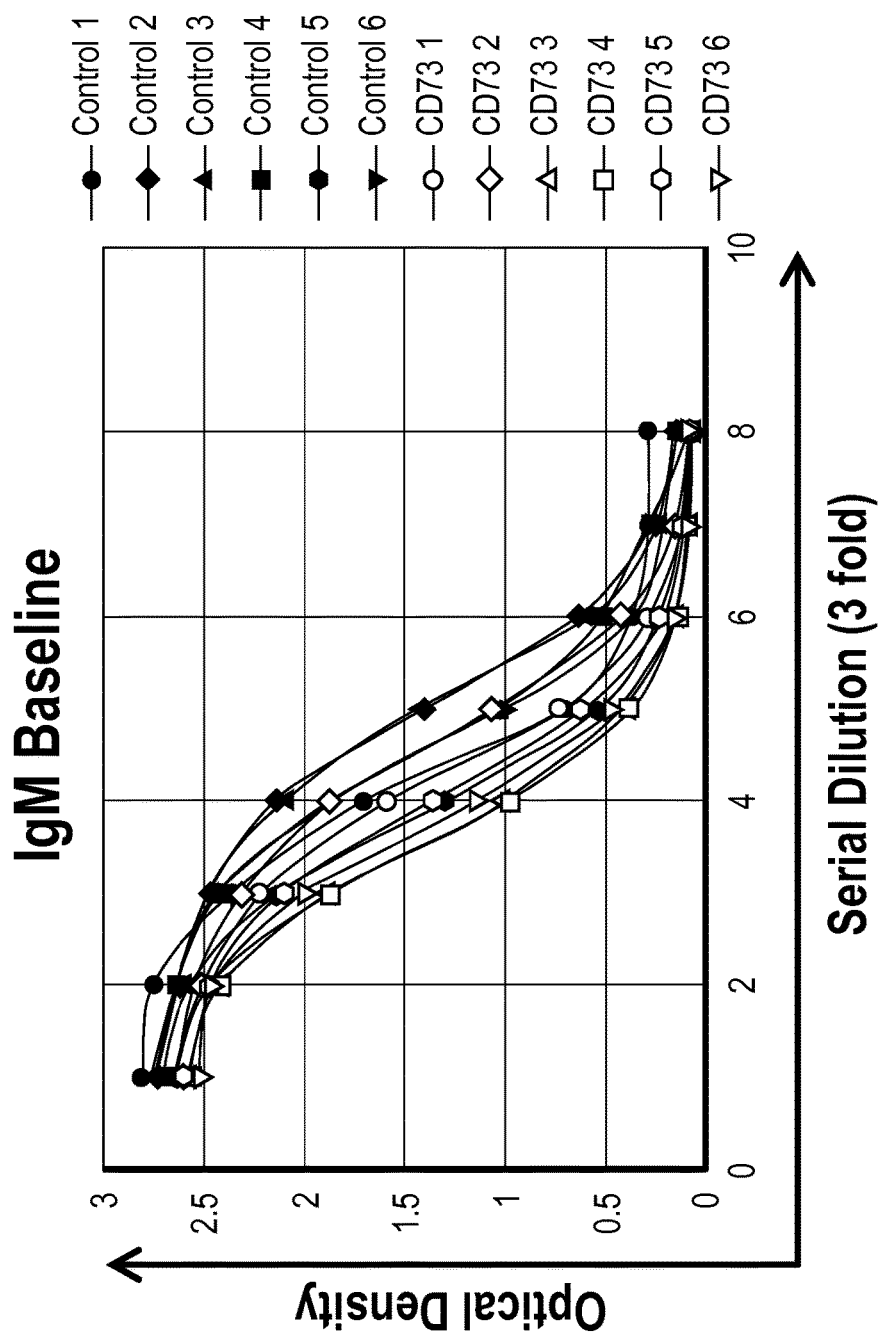
FIG. 4A is a graph comparing the total IgM in serum from unimmunized CD73 knockout mice (red) and the total IgM in serum from unimmunized control mice (blue).
Figure 4B:
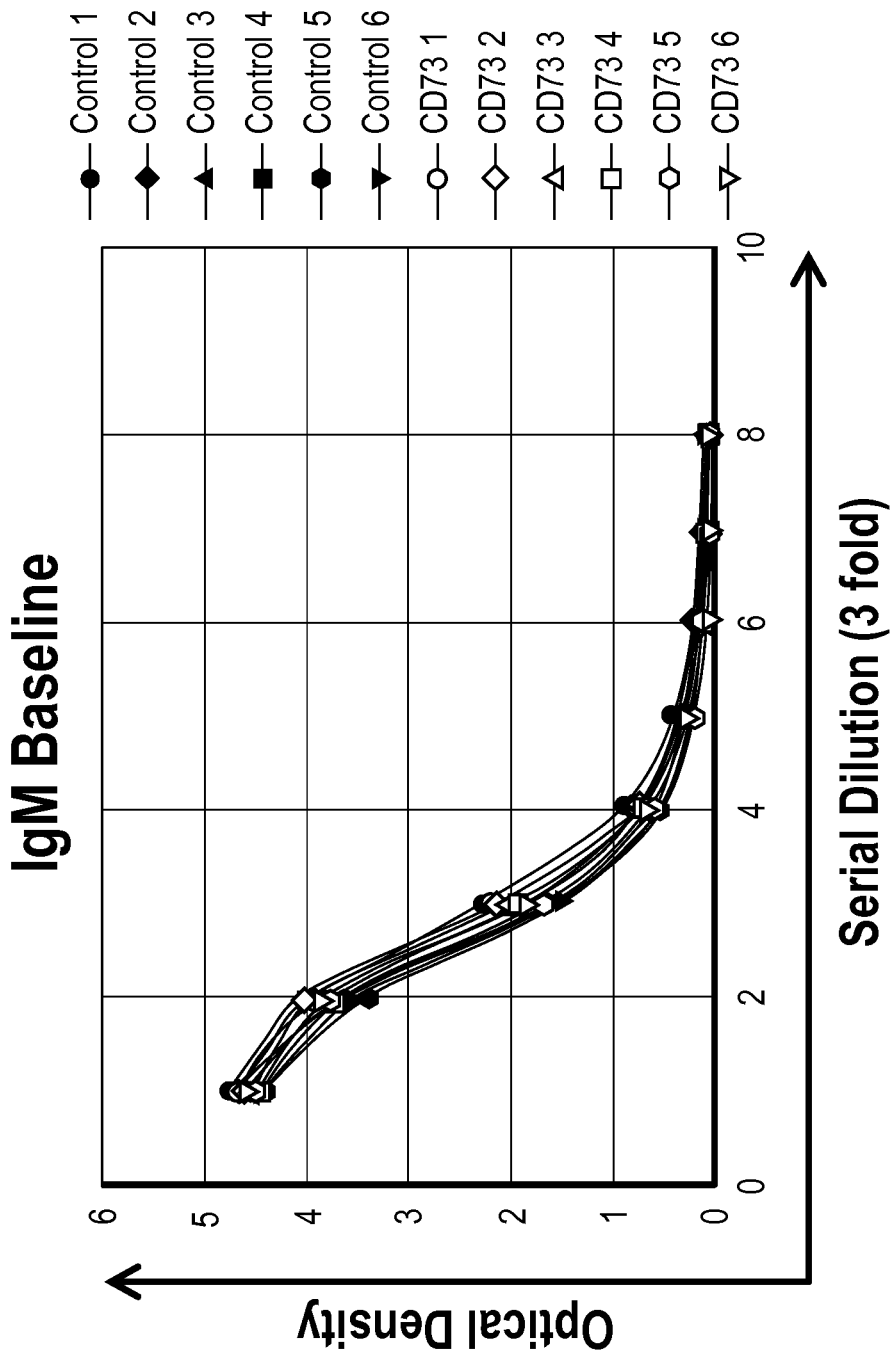
FIG. 4B is a graph comparing the total IgA in serum from unimmunized CD73 knockout mice (red) and the total IgA in serum from unimmunized control mice (blue).
Figure 4C:
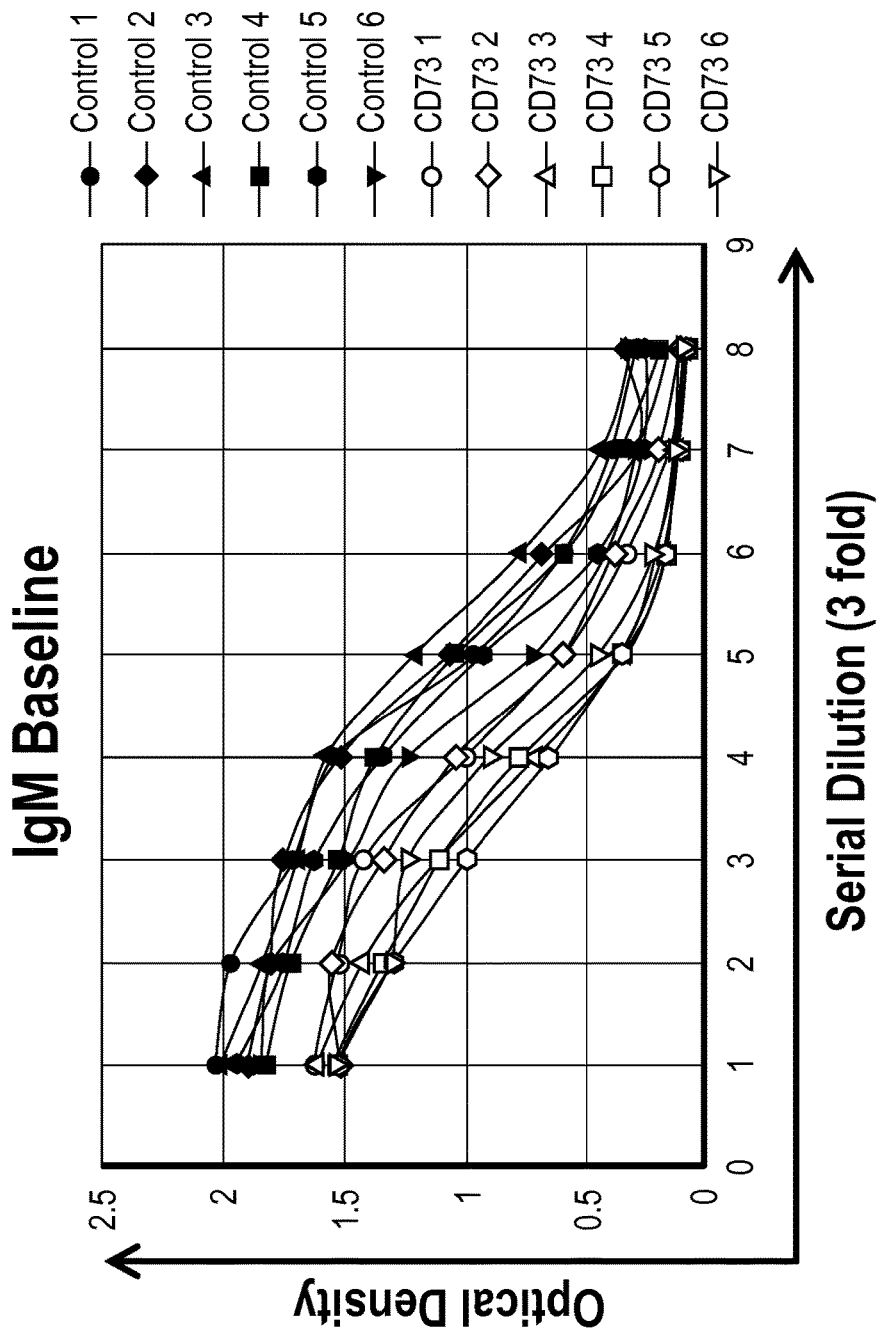
FIG. 4C is a graph comparing the total IgG in serum from unimmunized CD73 knockout mice (red) and the total IgG in serum from unimmunized control mice (blue).

CD73 is an enzyme upstream of A2b adenosine receptors that convert AMP into adenosine. The adenosine activates both the A2a and A2b adenosine receptors. As compared to normal control mice, CD73 knockout mice had a 3 fold reduction in IgG in serum (FIG. 4C), but IgA was not significantly reduced (FIG. 4B). The IgM levels of the control and CD37 knockout mice were similar (FIG. 4A).

Figure 5A:
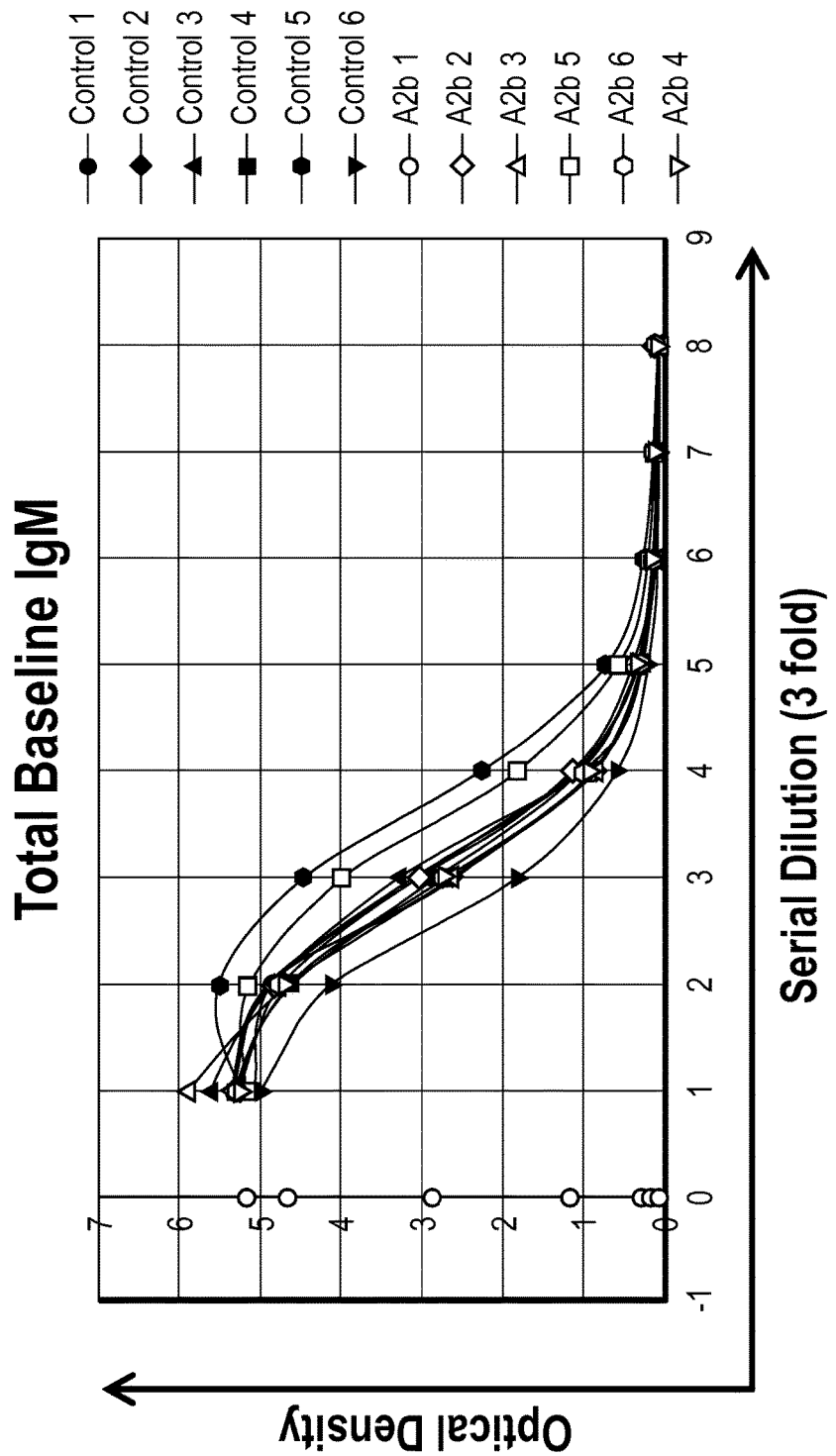
FIG. 5A is a graph comparing the total IgM in serum from unimmunized A2b adenosine receptor knockout mice (red) and the total IgM in serum from unimmunized control mice (blue).
Figure 5B:
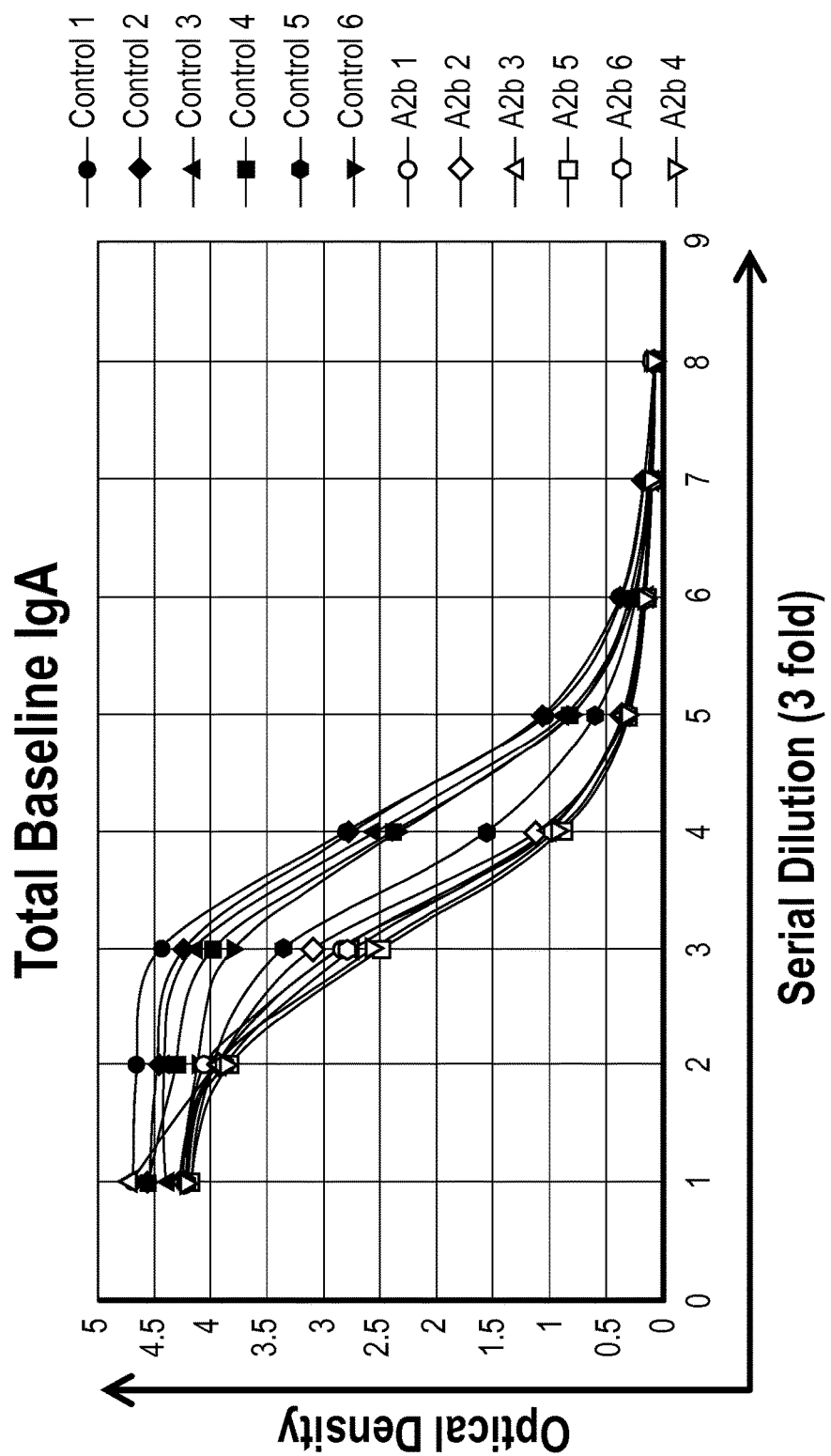
FIG. 5B is a graph comparing the total IgA in serum from unimmunized A2b adenosine receptor knockout mice (red) and the total IgA in serum from unimmunized control mice (blue).
Figure 5C:
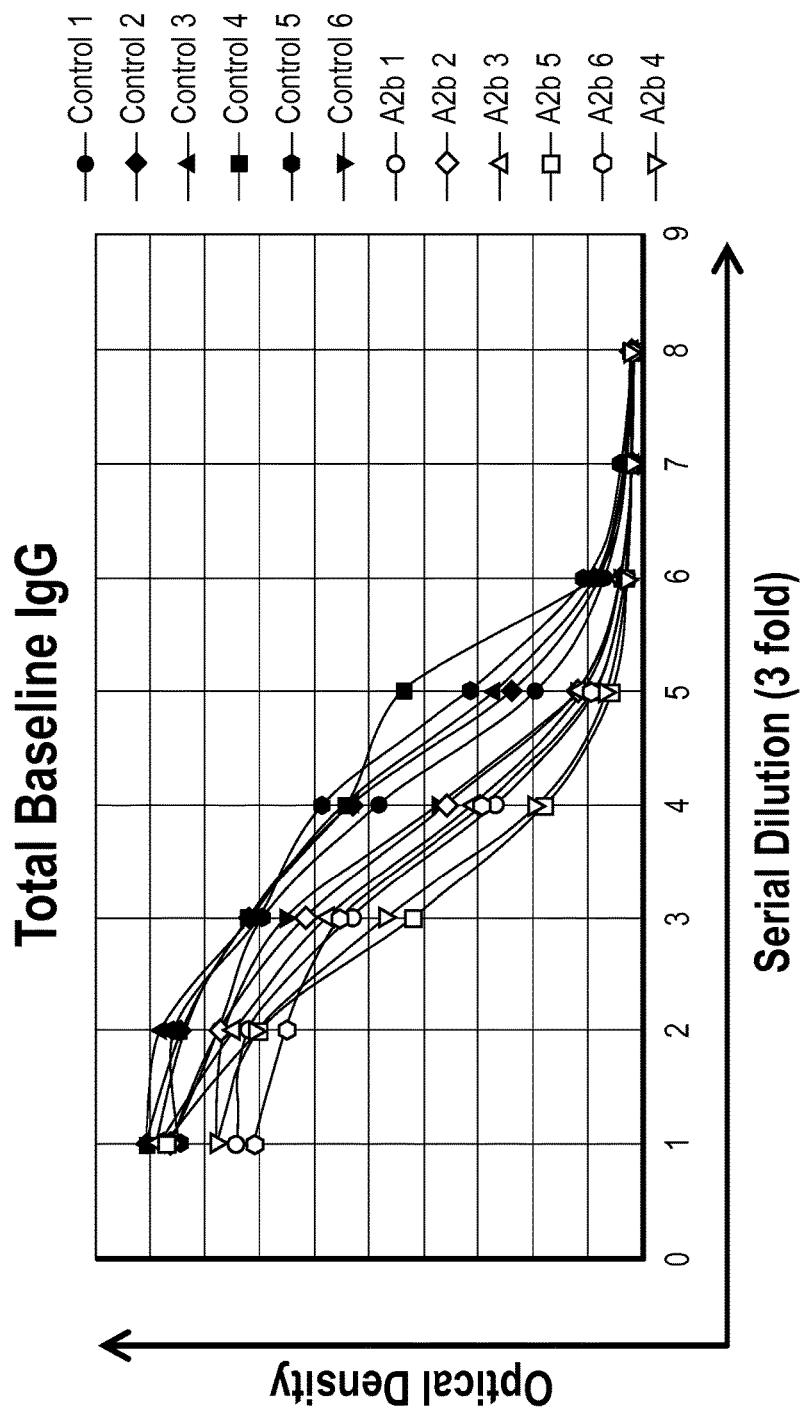
FIG. 5C is a graph comparing the total IgG in serum from unimmunized A2b adenosine receptor knockout mice (red) and the total IgG in serum from unimmunized control mice (blue).
Figure 6A:
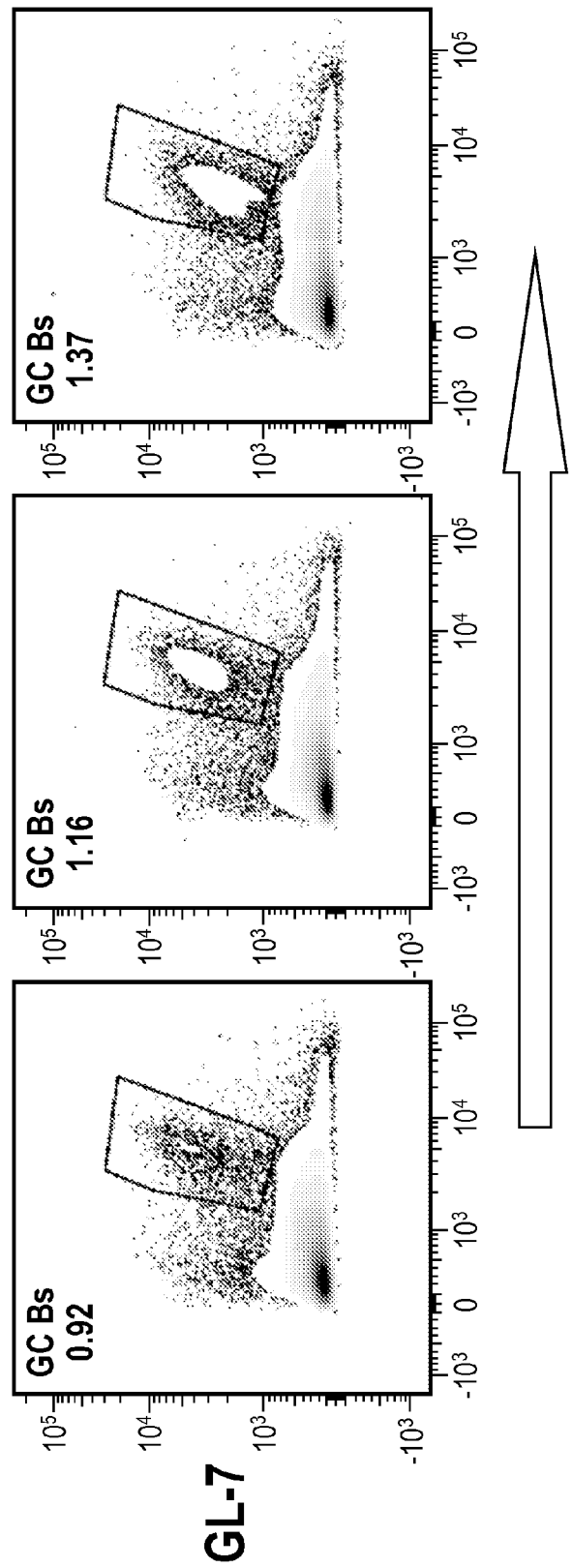
FIG. 6A are charts showing germinal center frequency in wild type mice.
Figure 6B:
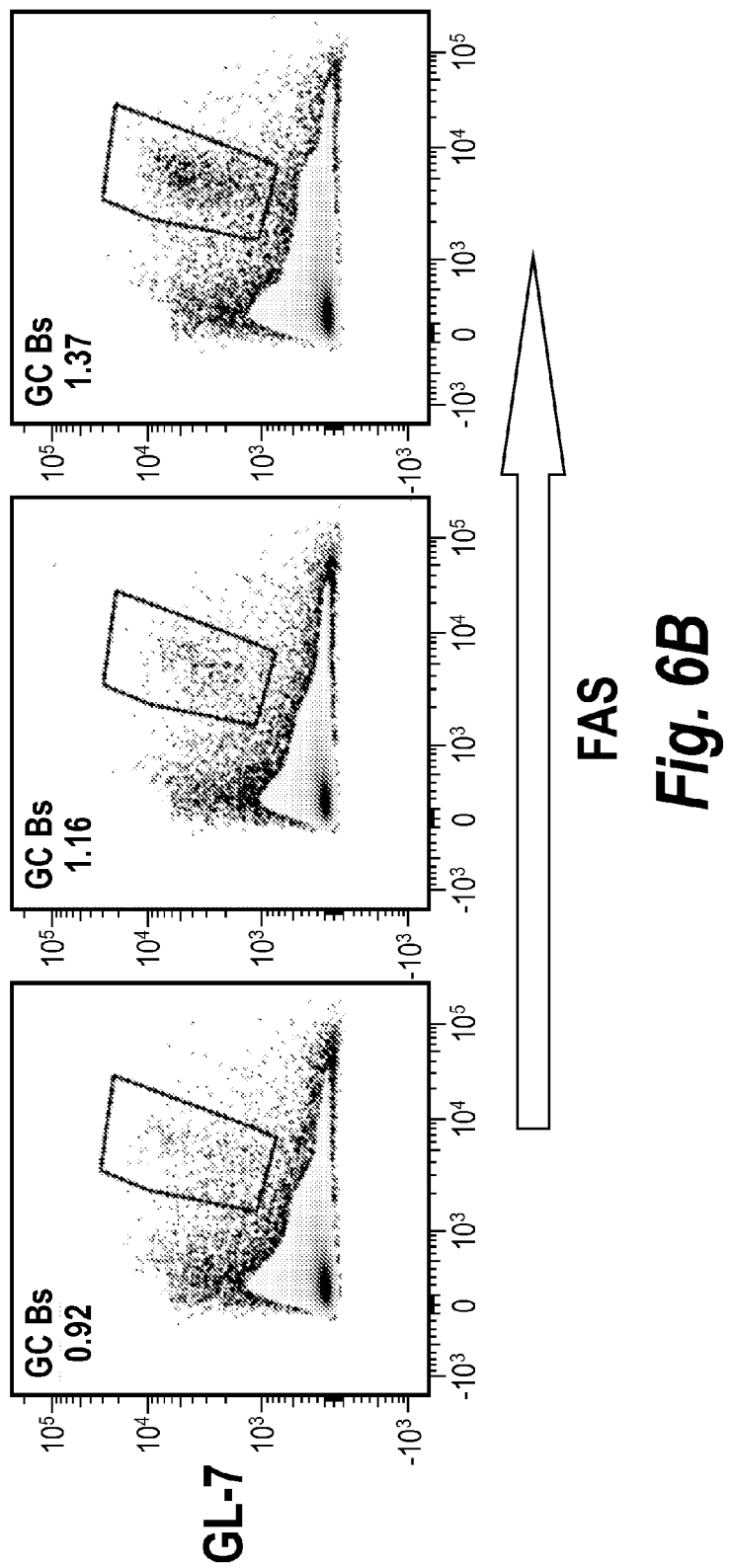
FIG. 6B are charts showing germinal center frequency in A2b adenosine receptor knockout mice.

Compared to normal control mice, A2b adenosine receptor knockout mice have similar IgM levels, a 3 fold reduction in IgG, and a 3-6 fold reduction in IgA in total serum as (FIGS. 5A-5C). The decrease in IgG and IgA coupled with the similar levels of IgM in the A2b adenosine receptor knockout mice indicates that A2b adenosine receptors have a role in class switch recombination. Additionally, it was observed that mice that lack A2b adenosine receptors have a 5 to 10 fold reduction in the frequency of germinal center B cells (FIG. 6A-B). There was also a reduction in class switched memory B cells in the spleen and bone marrow (data not shown).

Figure 7A:
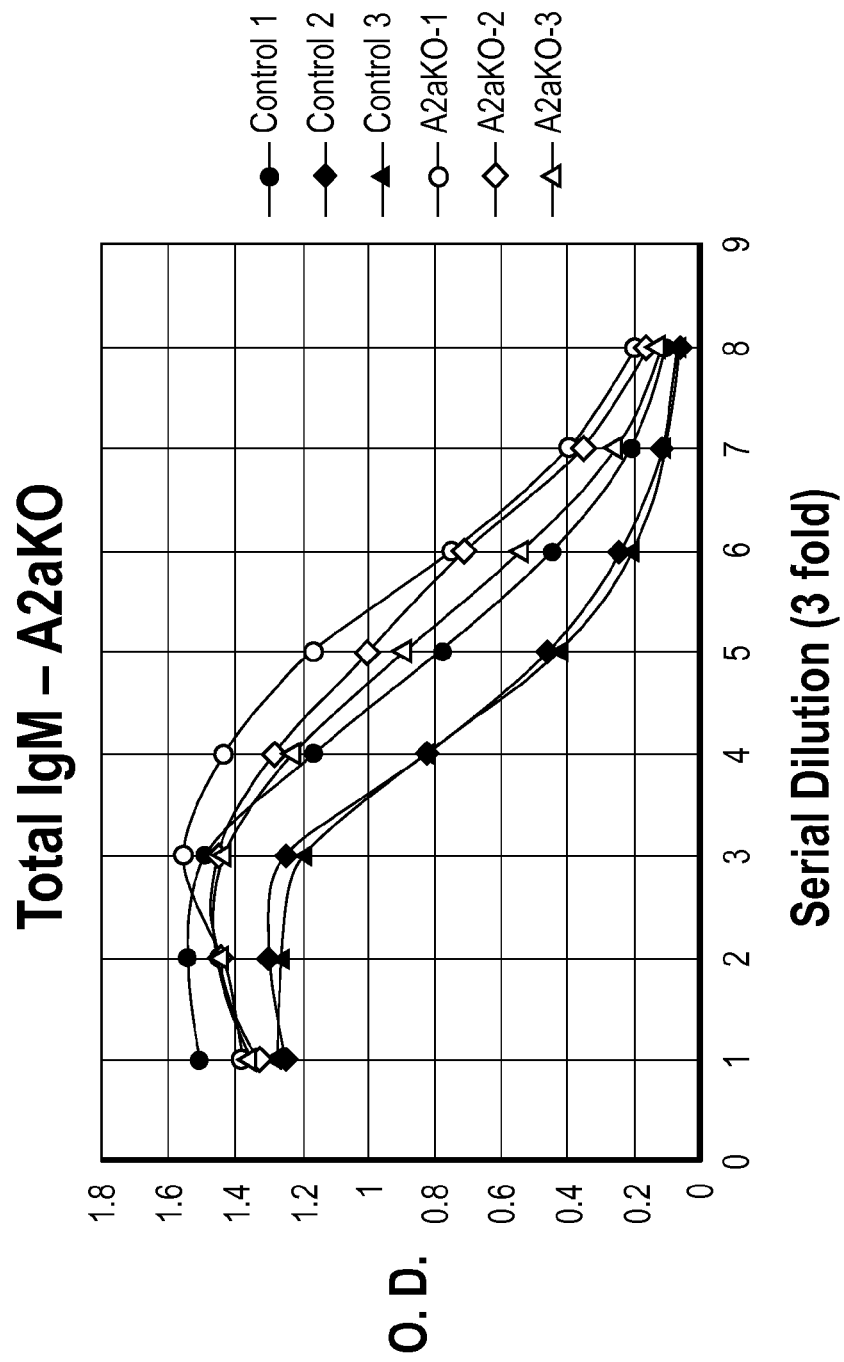
FIG. 7A is a chart showing total serum IgM from WT C57B/6 mice and A2a adenosine receptor knockout was assessed for total serum IgM. Knockout mice depicted as red lines, WT as Blue lines. Serial 3 fold dilutions on the x axis, optical density is on the y axis.
Figure 7B:
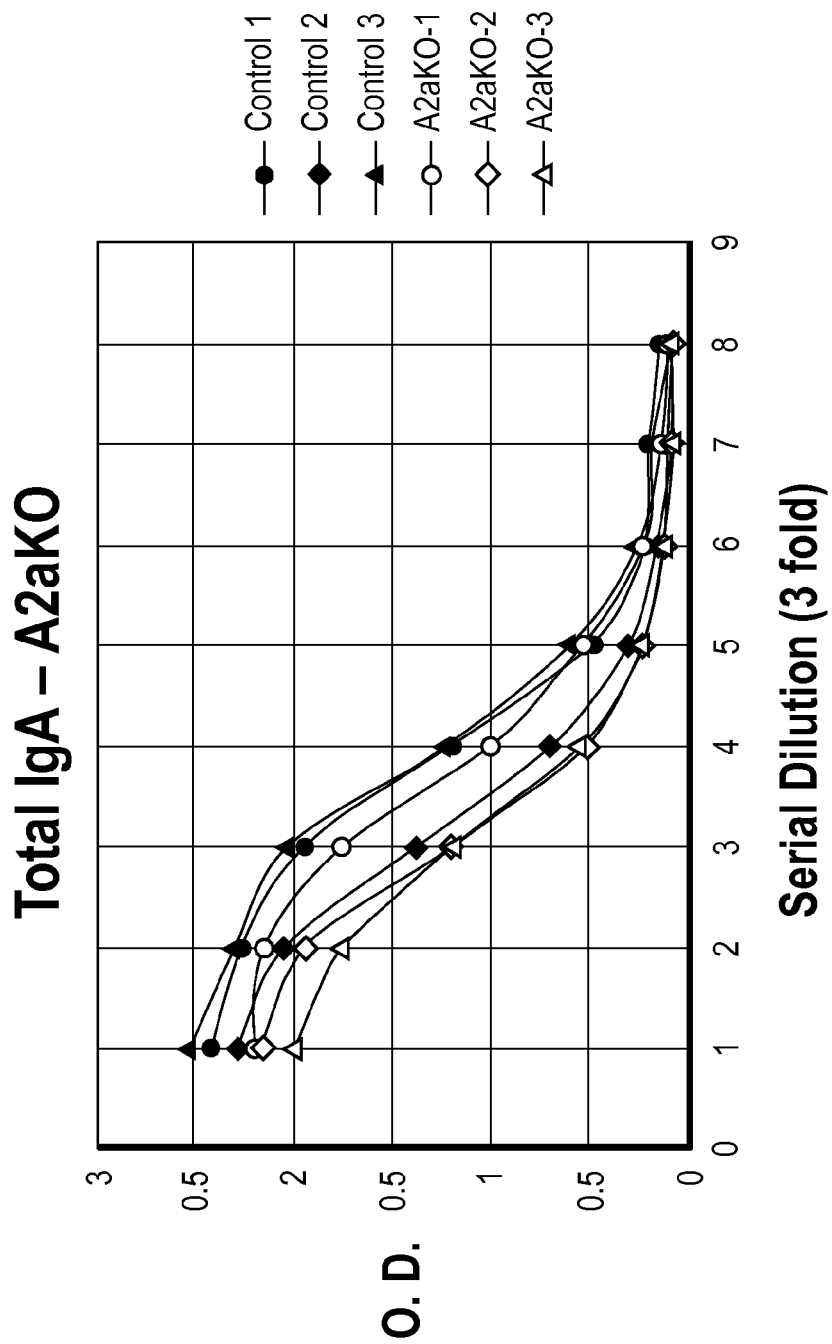
FIG. 7B is a chart showing total serum IgA from WT C57B/6 mice and A2a adenosine receptor knockout was assessed for total serum IgA. Knockout mice depicted as red lines, WT as Blue lines. Serial 3 fold dilutions on the x axis, optical density is on the y axis.
Figure 9A:
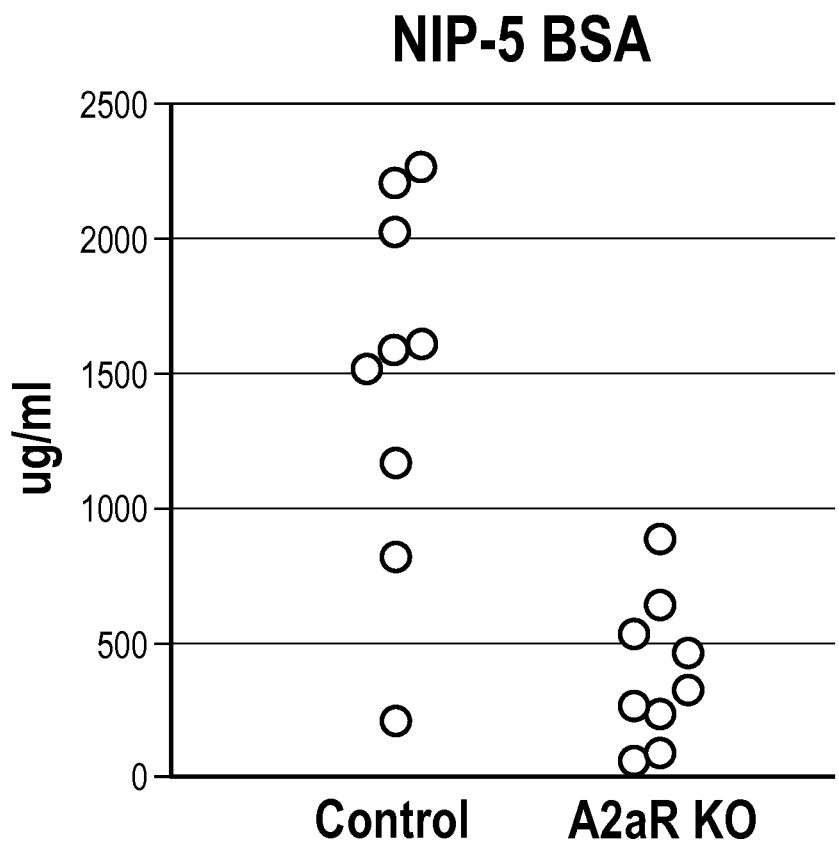
FIG. 9A is a chart showing the amount of antigen specific IgG in each mouse as measured by NIP-5-BSA, 50 days post immunization with NP-OVA/Alum for both A2a adenosine knockout mice and wild type controls.
Figure 9B:
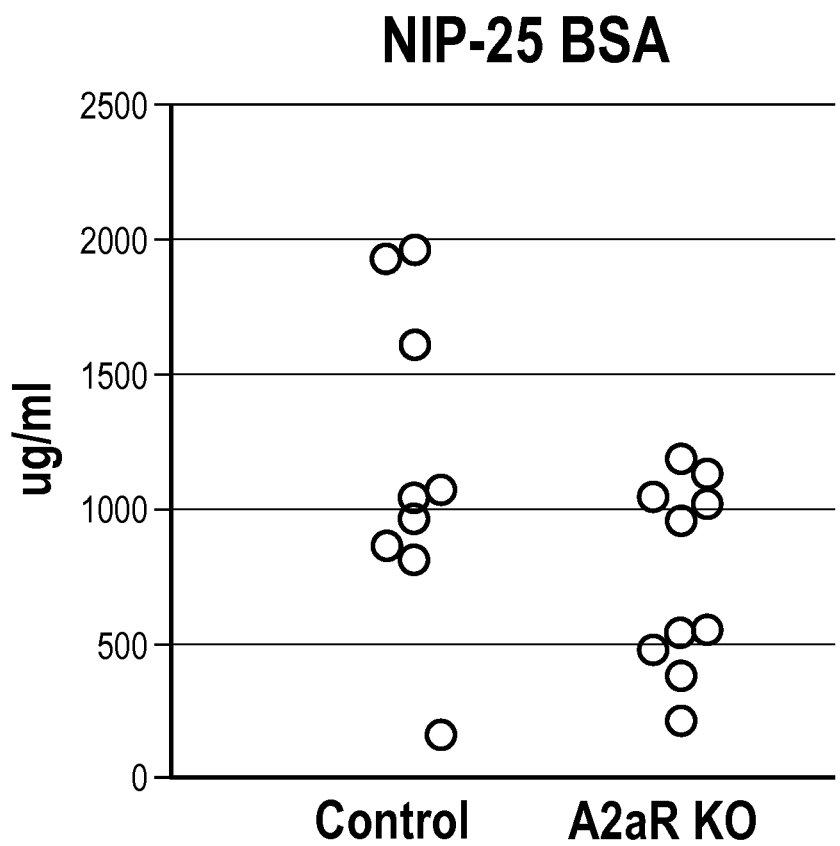
FIG. 9B is a chart showing the amount of antigen specific IgG in each mouse as measured by NIP-25-BSA, 50 days post immunization with NP-OVA/Alum for both A2a adenosine knockout mice and wild type controls.
Figure 9C:
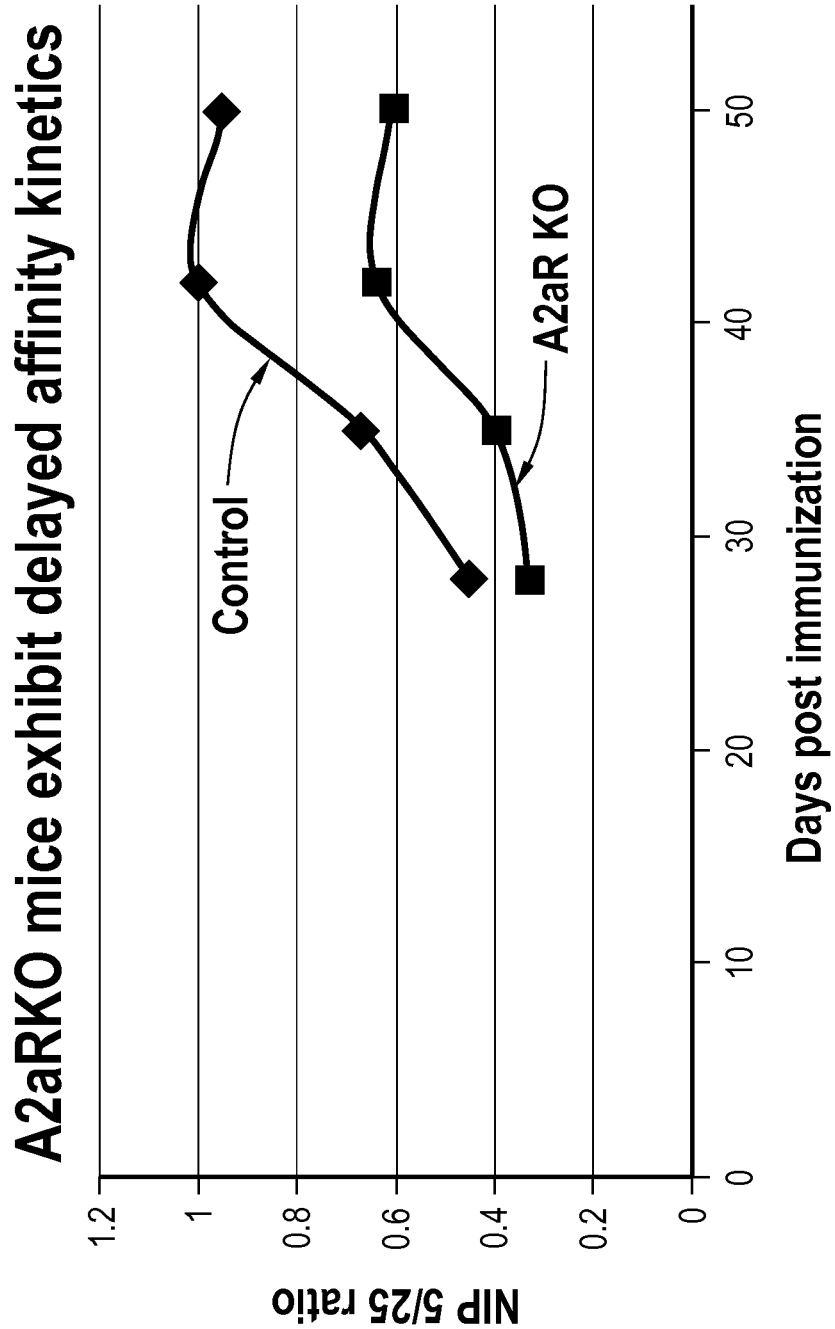
FIG. 9C is a chart comparing the affinity kinetics of immunized A2a adenosine receptor knockout mice to control mice.
Figure 9D:
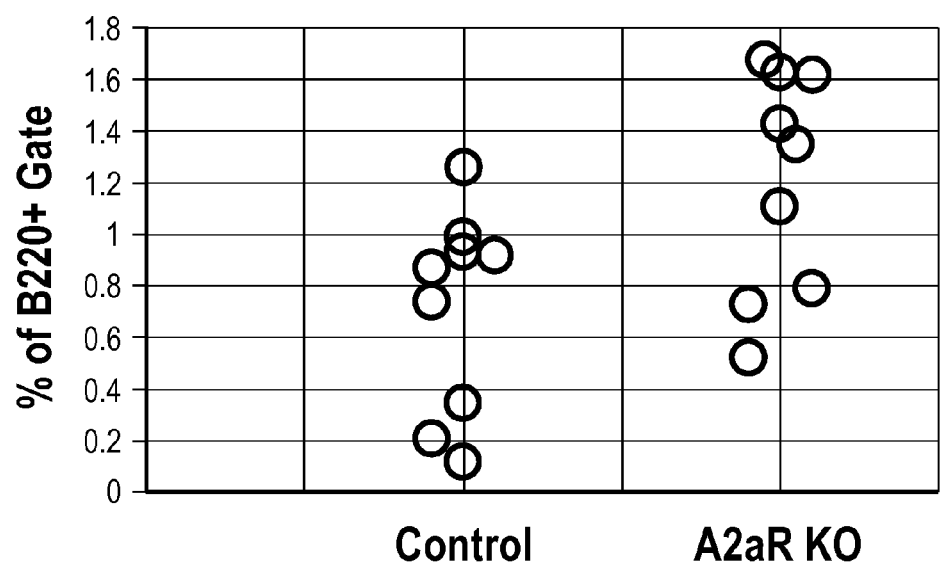
FIG. 9D is a chart comparing B cell frequency in the germinal center between A2a adenosine receptor knockout mice to control mice as determined by flow cytometry, 64 days after immunization of A2a adenosine receptor knockout mice and control mice with NP-OVA/Alum.
Figure 9E:
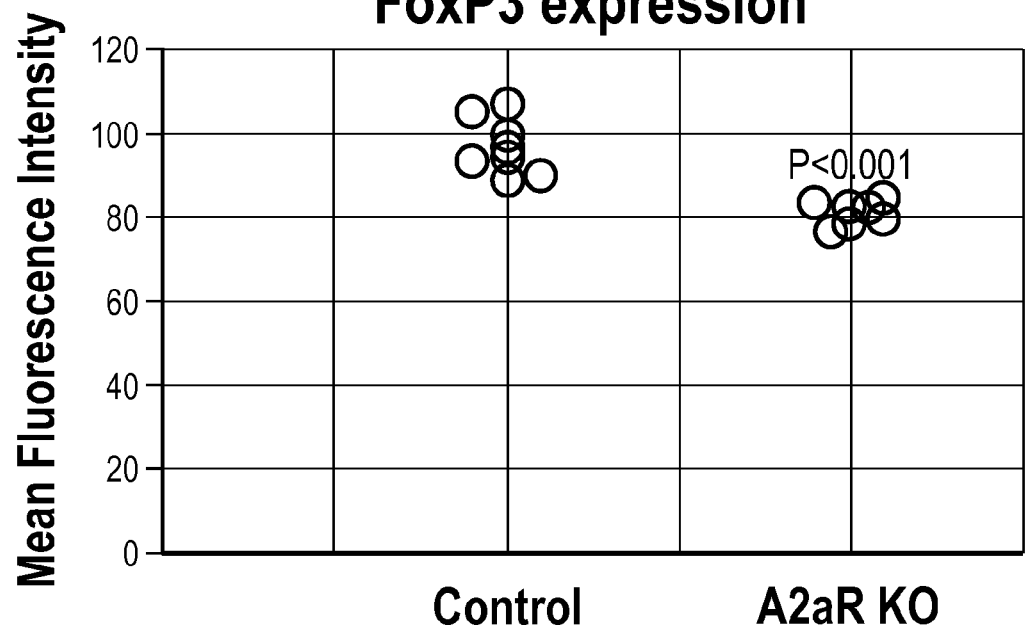
FIG. 9E is a chart comparing the expression levels of FoxP3 transcription factor between A2a adenosine receptor knockout mice to control mice assessed by flow cytometry, 64 days following immunization.

There was no difference in plasma levels of IgG or IgA in A2a adenosine receptor knockout mice as compared to control (new FIG. 7A-7C). This result indicated that A2a adenosine receptor was not directly involved in class switch recombination. However, upon immunization with a NP-OVA antigen, the A2a adenosine receptor knockout mice had impaired ability to generate high affinity antibodies (e.g., NIP-5-BSA) and impaired affinity maturation (FIGS. 9A-9B). The immunized A2a adenosine receptor knockout mice had increased frequency of total and antigen specific germinal center B cells 63 days after immunization with NP-OVA (FIG. 9C). Additionally, the immunized A2a adenosine receptor knockout mice had reduced expression of transcription factor FoxP3 in T follicular regulatory cells (FIG. 9D). FOXP3 is a key transcription factor in the development and function of T follicular regulatory cells, which are important in collapsing and regulating the germinal center reaction. These results indicate that adenosine A2a receptors play a role in the efficient resolution of the germinal center reaction and possibly selection of high affinity B cell clones.

The results show that extracellular adenosine generated by CD73 and subsequent signaling through A2a/A2b adenosine receptors potentiates germinal center maintenance and class switching of antibodies. Accordingly, these results demonstrate that activation of A2a/A2b adenosine receptors is useful for enhancing the effects of vaccination.

Example 5. Stimulation of A2a Adenosine Receptors Accelerates Development of High Affinity Antibodies This example shows that stimulation of A2a adenosine receptors at the germinal center post vaccination increases production of high affinity antigen specific antibodies.

Method

Immunized mice (as described in Example 1) were treated with the A2a specific agonist, CGS-21680, via subcutaneous injections once or twice daily at a dose of 1 mg/kg during various time points during the germinal center reaction.

A2a adenosine receptor agonist, CGS-21680 (Tocris), was re-suspended as a 50 mM stock solution in DMSO and stored at −20 degrees. The CGS-21680 solution was re-suspended in Hanks balanced salt solution (HBSS)(Gibco) to a dosage of 1 mg/kg.

Four different experiments were performed to assay the effects of CGS-21680 as described above.

1) Five immunized mice were treated with 5 subcutaneous injections of CGS-21680 (two on 4 days after immunization, two 5 days after immunization, and one 6 days after immunization). Five untreated mice were used as controls (treated with 1:600 dilution of DMSO in HBSS). All mice were sacrificed on day 6.

2) Five immunized mice were treated with 7 subcutaneous injections of CGS-21680 (two on 9 days after immunization, two 10 days after immunization, two 11 days after immunization, and one 12 days after immunization). Five untreated mice were used as controls (treated with 1:600 dilution of DMSO in HBSS). All mice were sacrificed on day 12.

3) Ten immunized mice were treated with twice daily subcutaneous injections of CGS-21680 on day 8-20 after immunization and one treatment on day 21 after immunization. Ten untreated mice were used as controls (treated with 1:600 dilution of DMSO in HBSS). All mice were sacrificed on day 21.

4) Ten immunized mice were treated with twice daily subcutaneous injections of CGS-21680 on day 8-41 after immunization and one treatment on day 42 days after immunization. Ten untreated mice were used as controls (treated with 1:600 dilution of DMSO in HBSS). All mice were sacrificed on day 42.

During Experiment 4, mice were bled once every week via retro-orbital eye bleed discussed above in Example 4.

Serum from Experiment 4 was subjected to ELISA analysis.

Flow cytometric analysis of germinal center B cells from Experiment 1 (gated as lymphocytes, B220+, Gl-7 positive, CD38 negative; FIGS. 10E and 10F) and Experiment 3 (B220 positive, Gl-7 hi, IgD-negative; FIG. 10D) was performed. The flow cytometric analysis was performed according to the protocol discussed in Example.

Results

Figure 10A:
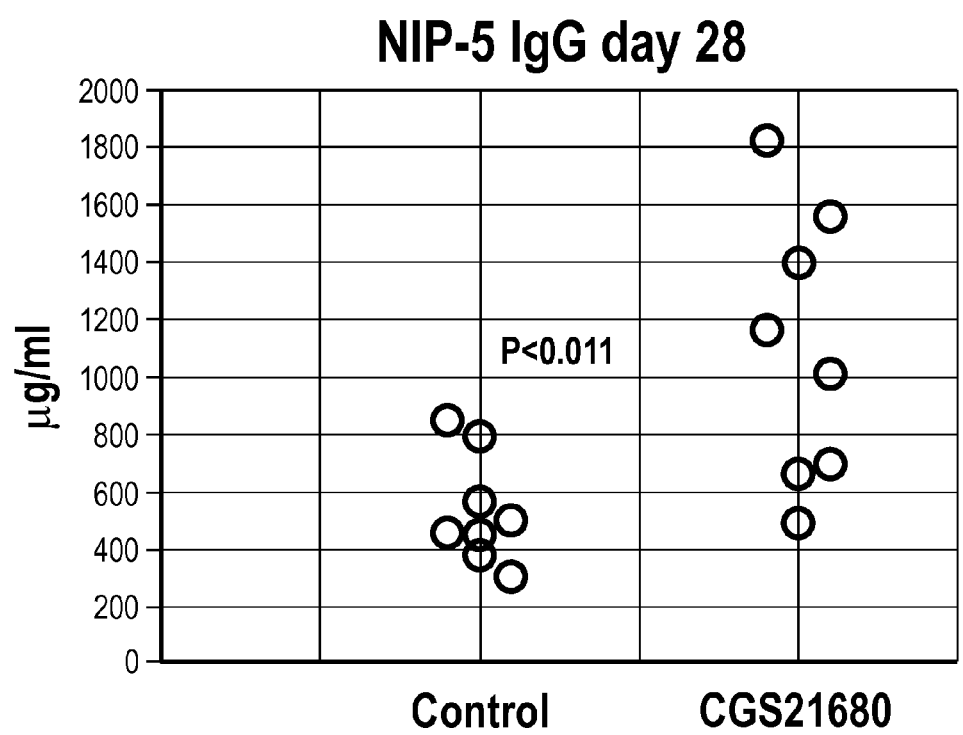
FIG. 10A is a chart showing the concentration of NIP-5 is the serum of each mouse treated with A2a adenosine receptor agonist, CGS21680 as compared to the concentration of NIP-5 is the serum of each control mouse, 28 days following immunization.
Figure 10B:
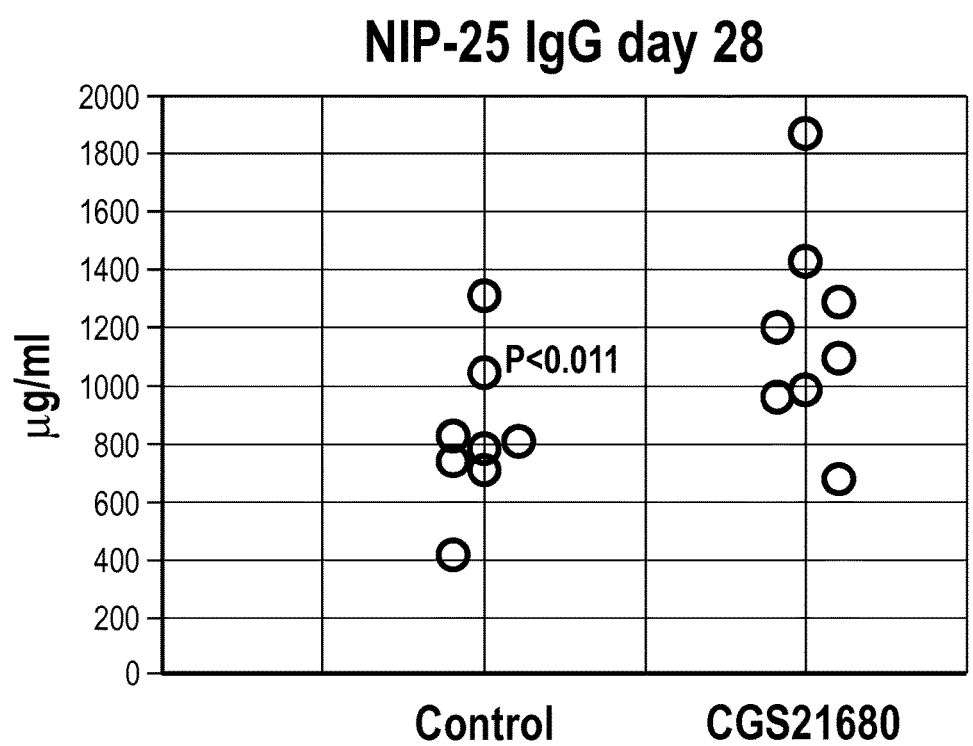
FIG. 10B is a chart showing the concentration of NIP-25 is the serum of each mouse treated with A2a adenosine receptor agonist, CGS21680 as compared to the concentration of NIP-5 is the serum of each control mouse, 28 days following immunization.
Figure 10C:
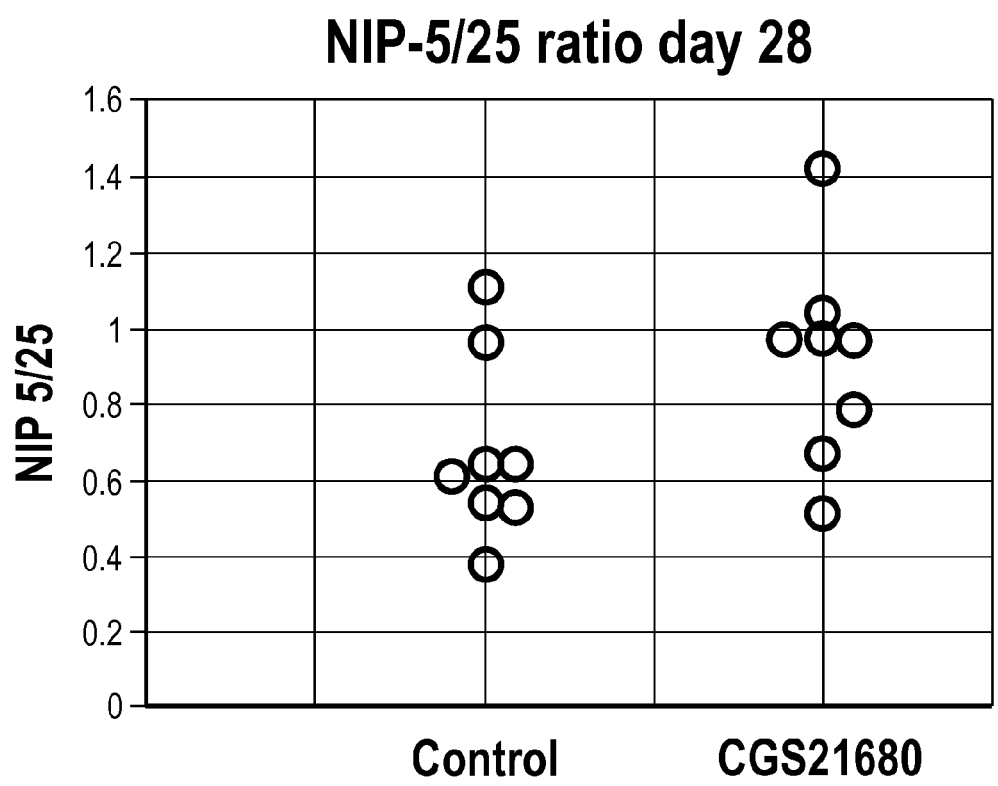
FIG. 10C is a chart showing the ratio of NIP 5 to NIP 25 antibody in each mouse treated with CGS21680 as compared to the ratio of NIP 5 to NIP 25 antibody in each control mouse.
Figure 10D:
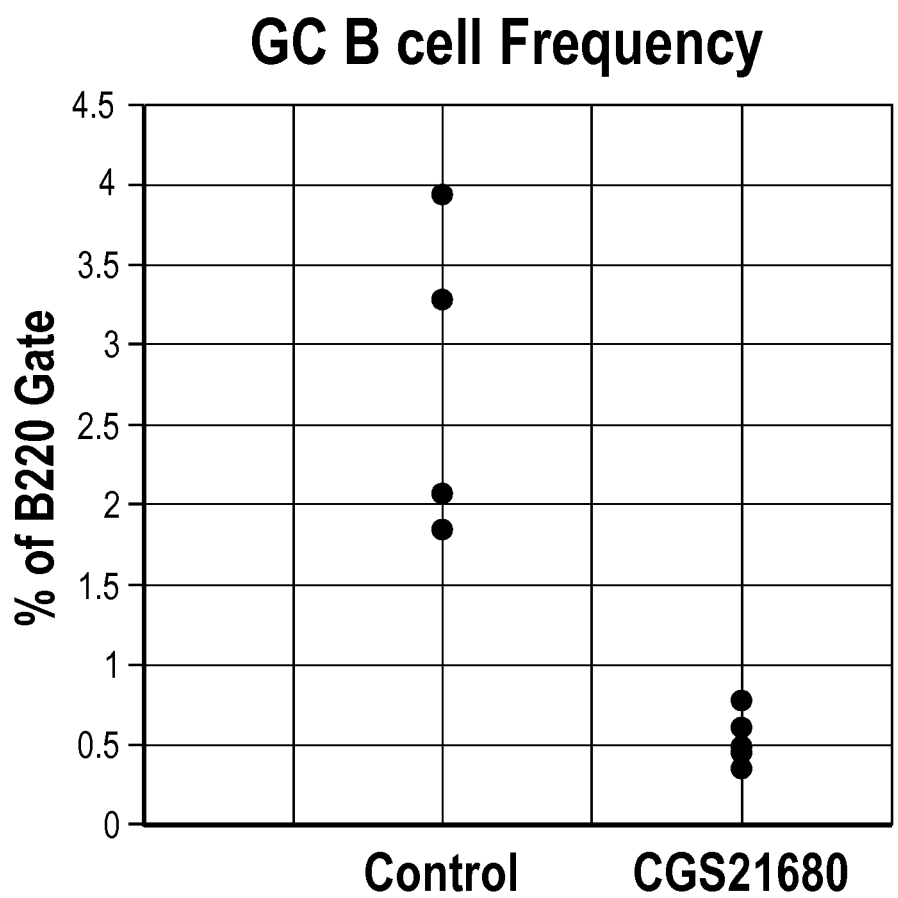
FIG. 10D is a chart showing germinal center frequency of B cells in mice treated with CGS21680 as compared to control.
Figure 10E:
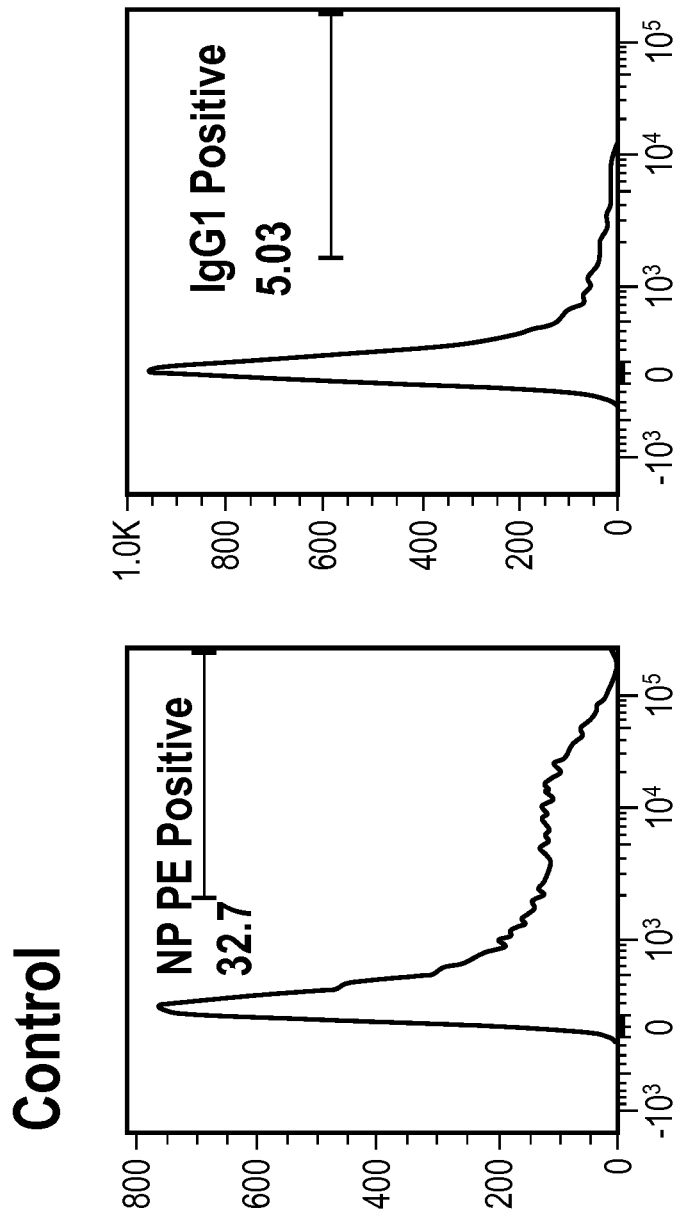
FIG. 10E are graphs showing that germinal center B cells not treated with CGS21680 have less class switching antigen specific germinal center B cells.
Figure 10F:
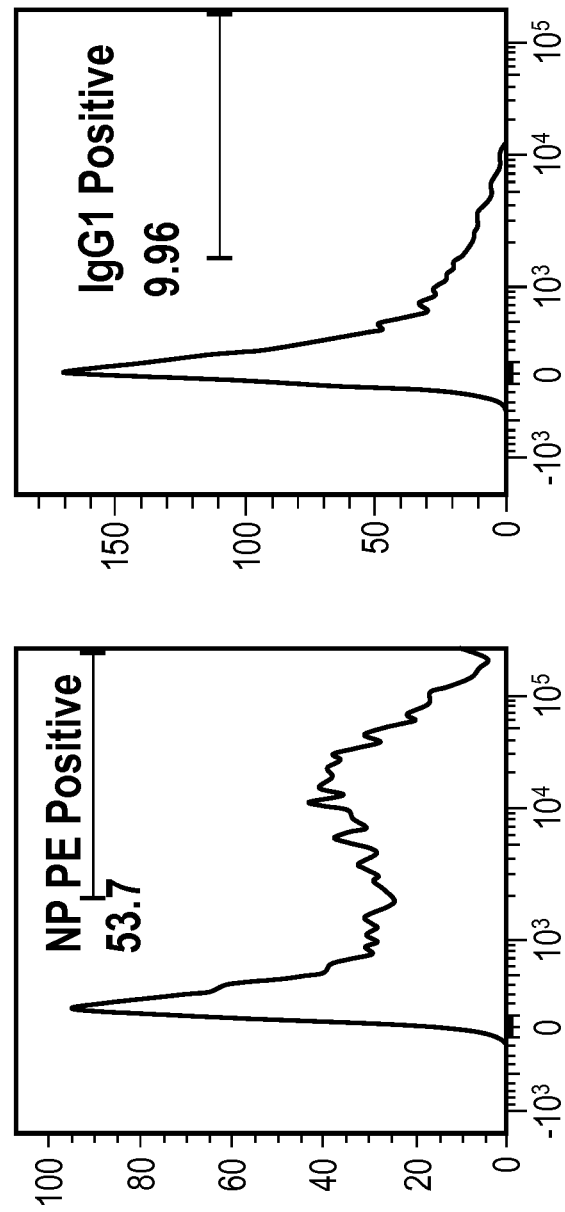
FIG. 10F are graphs showing that germinal center B cells treated with CGS21680 have enhanced class switching antigen specific germinal center B cells.

The ELISA analysis of mice treated with CGS21680 from Experiment 4 showed that there was an accelerated appearance of high affinity anti-NIP-5 serum IgG antibody on day 28 following immunization (FIG. 10A). The serum for mice treated with CGS21680 from Experiment 4, was also assayed by ELISA for total antigen specific NIP-25, which includes both high and low affinity antigen specific IgG, (FIG. 10B). The ratio of NIP-5/25 antibody detected by ELISA in mice treated with CGS21680 (see FIGS. 10A and 10B) was used as a measurement of affinity maturation. Over the course of immunization the NIP-5/25 ratio should approach 1.0 showing that all the antigen specific antibodies are high affinity antibodies. Mice treated with CGS21680 showed accelerated affinity kinetics as the NIP-5/25 ratio increased (FIG. 10C).

Stimulation of A2a adenosine receptor with CGS-21680 in Experiment 3 lead to a decrease in the frequency of germinal center B cells as compared to control as measured by flow cytometry (FIG. 10D). Flow cytometry analysis of Experiment 1 showed that stimulation of A2a adenosine receptor with CGS-21680 lead to an increased proportion of class switched IgG1 germinal center B cells and a higher amount class switched NP-PE binding cells (FIGS. 10E and 10F).

These results show stimulation of the A2a adenosine receptor enhances the class switching of antibodies in the germinal center. Accordingly, these results demonstrate that activation of A2a adenosine receptors is useful for enhancing the effects of vaccination by improving class switching.

Example 6. Adenosine Receptor Stimulation Accelerates Class Switch Recombination In Vitro This example shows that stimulation of A2a and A2b adenosine receptors on resting B cells accelerates class switch recombination in vitro.

Methods and Materials

Female C57 B/6 mice were sacrificed and spleens harvested and generated into single cell suspensions. Lymphocytes were isolated using Ficoll separation (GE Healthcare) and interface layer was collected after centrifugation (1000×g for 10 minutes). Cells were FC Blocked as described above and then stained with CD43 FITC (clone S7) and then washed and stained with anti-FITC microbeads (Miltenyi) at 4° C. for 30 minutes. Cells were then depleted using magnetic separation autoMACS deplete(s) program (Miltenyi). The depleted fraction was used for experiments as these consist of resting B cells.

B cells plated in a 24 well plate at 200,000 cells pre well with IMDM media, as described in Example 3 (1 ml media/well). B cells were then stimulated using anti-CD40 antibody (2.5 μg/ml clone IC-10 eBiosciences) and recombinant mouse IL-4 (10 ng/ml, R&D). Wells were also stimulated with various doses of A2a and A2b adenosine receptor agonists (100 nM, 1 μM, and 10 μM NECA (A2a and A2b agonist) and 10 μm CGS21680 (A2a agonist)). All stimulating reagents were added at the seeding of the culture on day 0 and no other drugs were added thereafter.

After four days in culture, amount of class switch to IgG1 was determined by flow cytometric analysis by staining with anti-mouse IgM, IgG1, and B220. Plots are all gated on B220+ cells (FIG. 8A-8F)

Results

Figure 8A:
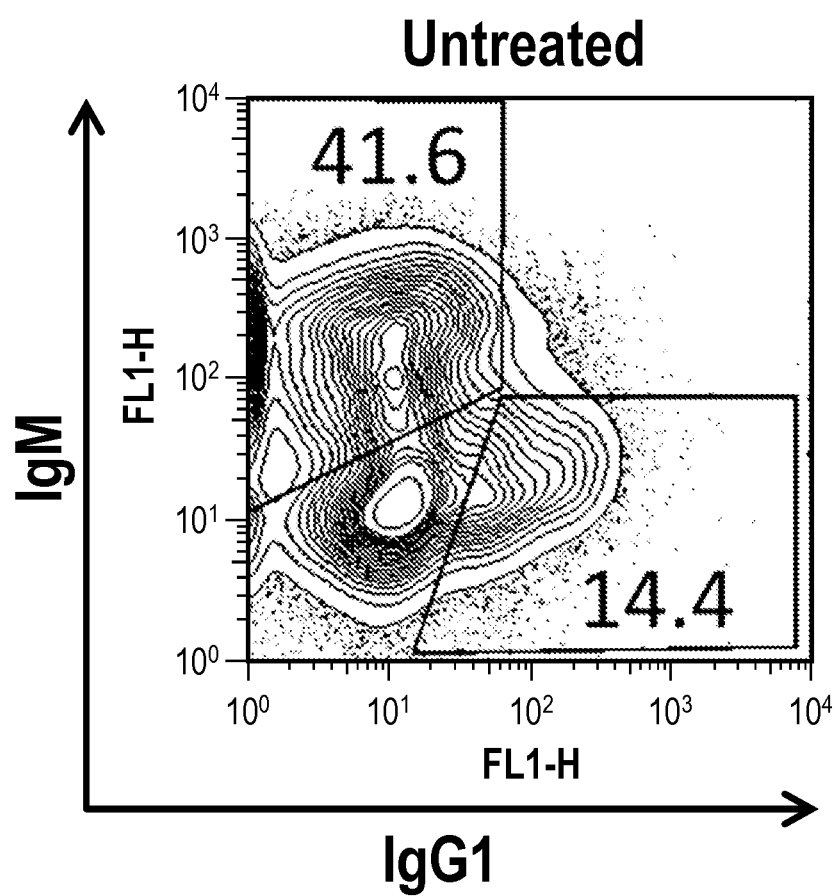
FIG. 8A is a diagram showing untreated B cells as a baseline to measure class switching of B cells stimulated with antibodies, growth factors, and A2a and/or A2B agonists.
Figure 8B:
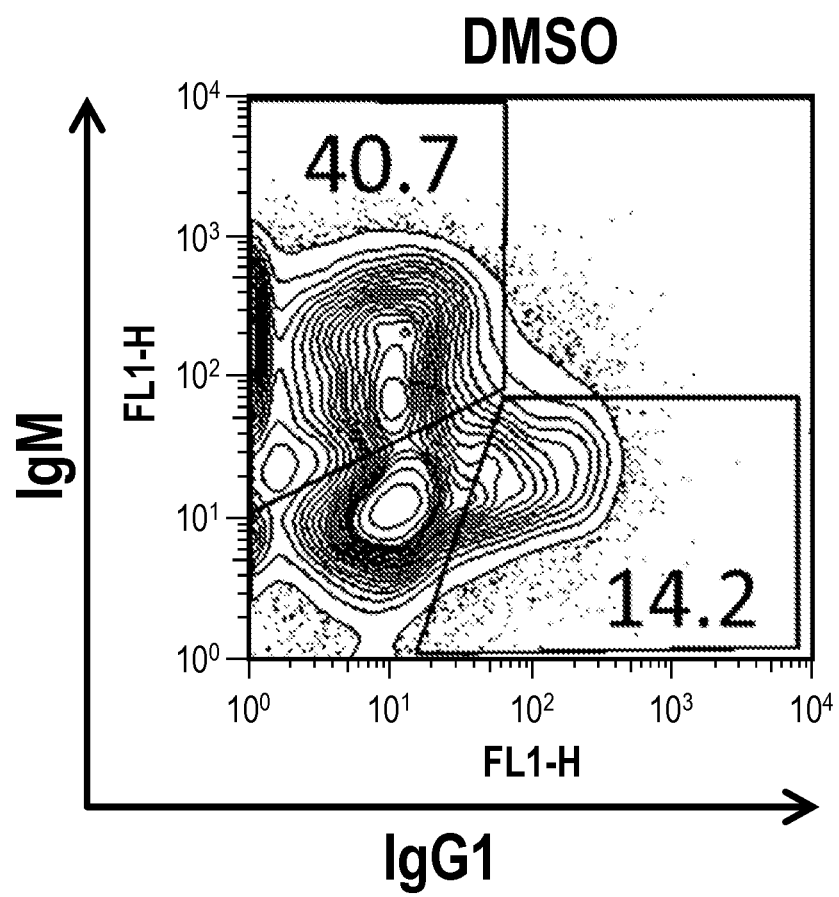
FIG. 8B is a diagram showing DMSO treated B cells have no class switching as compared to untreated B cells in FIG. 8A.
Figure 8C:
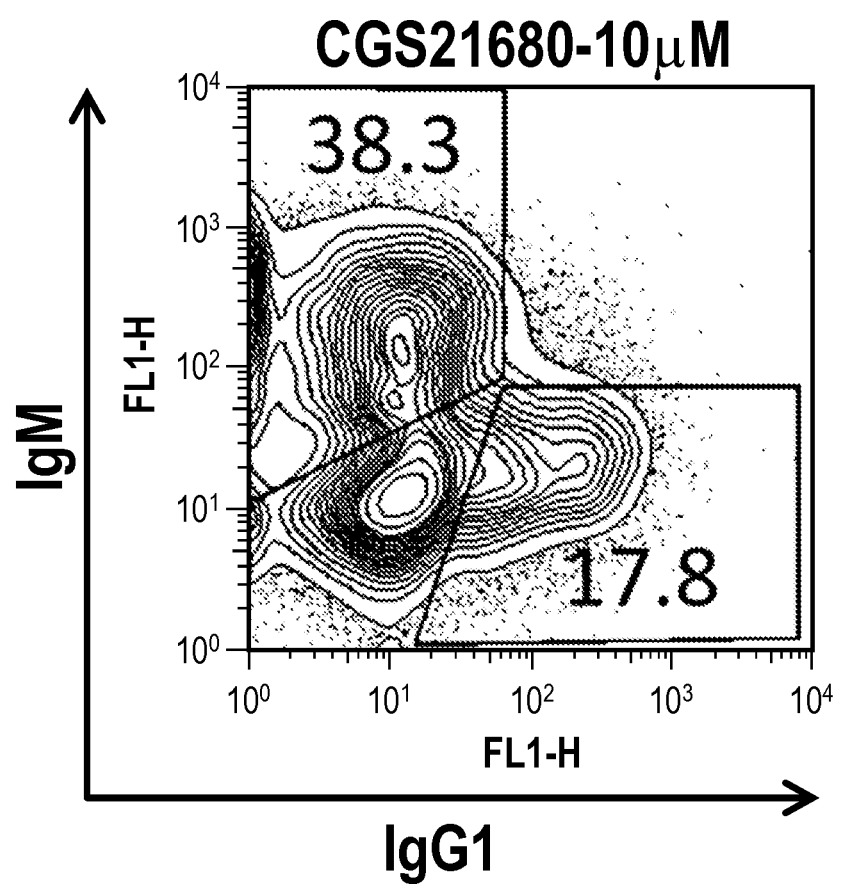
FIG. 8C is a diagram showing A2a adenosine receptor agonist, CGS21680, treated B cells at 10 µM has class switching as compared to untreated B cells in FIG. 8A.
Figure 8D:
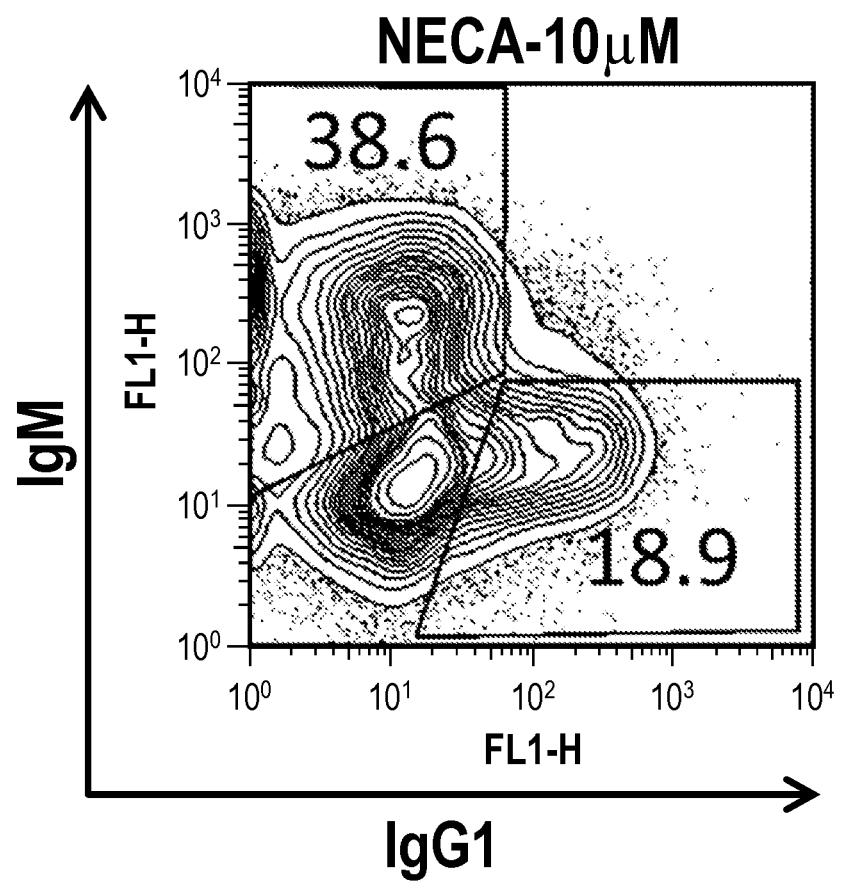
FIG. 8D is a diagram showing that A2a/A2b adenosine receptor agonist, NECA, treated B cells at 10 µM has class switching as compared to untreated B cells in FIG. 8A.
Figure 8E:
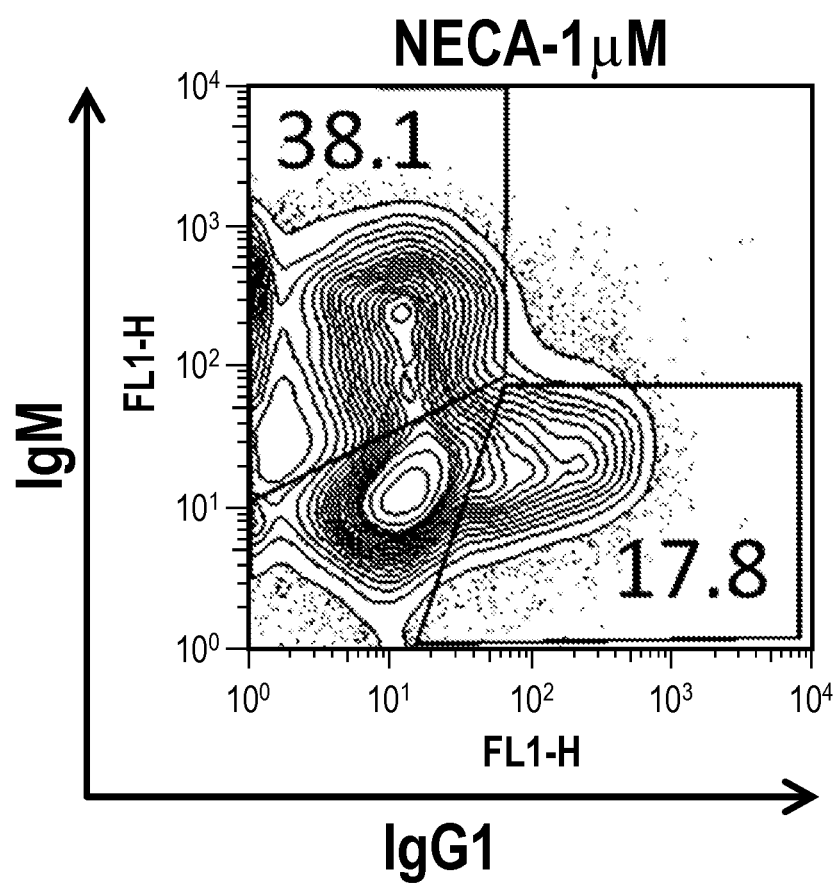
FIG. 8E is a diagram showing that A2a/A2b adenosine receptor agonist, NECA, treated B cells at 1 µM has class switching as compared to untreated B cells in FIG. 8A.
Figure 8F:
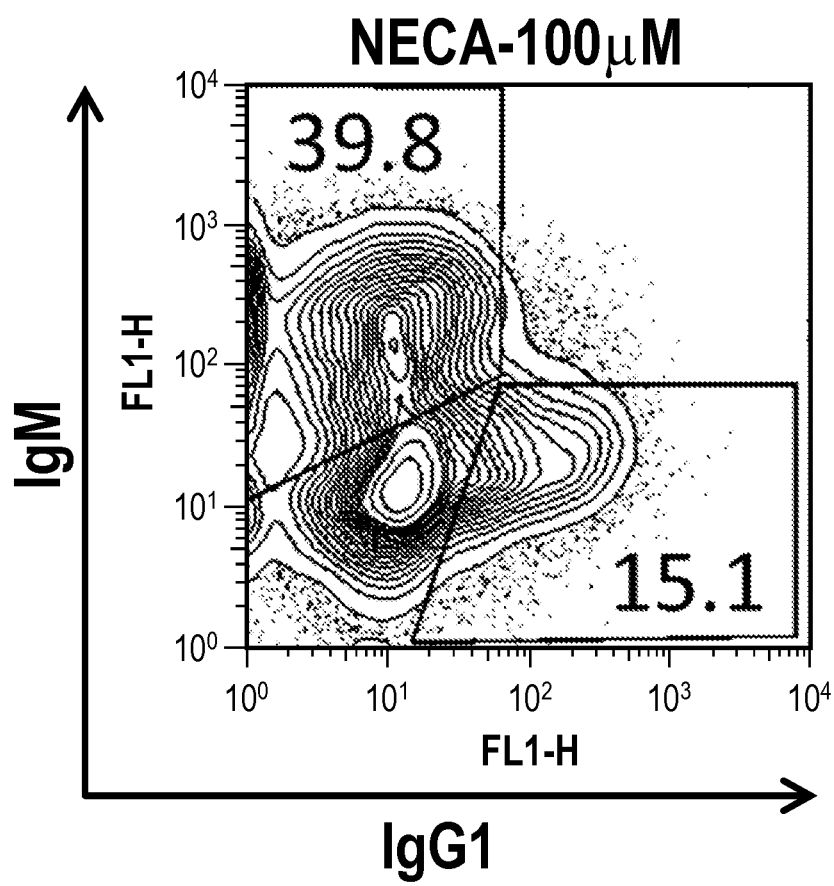
FIG. 8F is a diagram showing that A2a/A2b adenosine receptor agonist, NECA, treated B cells at 100 nM has class switching as compared to untreated B cells in FIG. 8A.

Enhanced class switching from native IgM to IgG1 is shown in groups treated with adenosine receptor agonists. FIG. 8A-B show that untreated and DMSO treated B cells have the nearly the same amounts of IgM and IgG1. Stimulation of both A2a and A2b adenosine receptors on B cells with NECA (FIG. 8D-8F) shows that 100 nM increases the class switching of IgM to IgG1 and that the class switching increases as the concentration of NECA increases.

FIG. old 8C shows a similar class switching increase of IgM to IgG1 with A2a adenosine receptor stimulation only using 10 µM of CGS21680.

The results show that stimulation of A2a and A2b adenosine receptors on B cells leads to the increase in class switching of B cells. Accordingly, the stimulation of A2a and A2b adenosine receptors is useful to enhance class switching of B cells, for example, after administration of a vaccine.

Example 7. A2a Adenosine Receptor Knockout Mice have an Enhanced Titer Post Vaccination This example shows that A2a adenosine receptor knockout mice have increased NIP-25 as compared to wild type mice after vaccination and subsequent immune boost/challenge.

Methods and Materials

Six male wild type C57 B/6 mice 10-12 weeks of age (controls) and six A2a adenosine receptor knockout mice of same age and sex of the control mice were immunized as described in Example 1. At day 21, the mice were given an immune boost of 1 µg NP-OVA with adjuvant via intraperitoneal injection. At day 42, the mice were given an immune challenge of 1 µg NP-OVA without adjuvant via tail vein injection.

Figure 11:
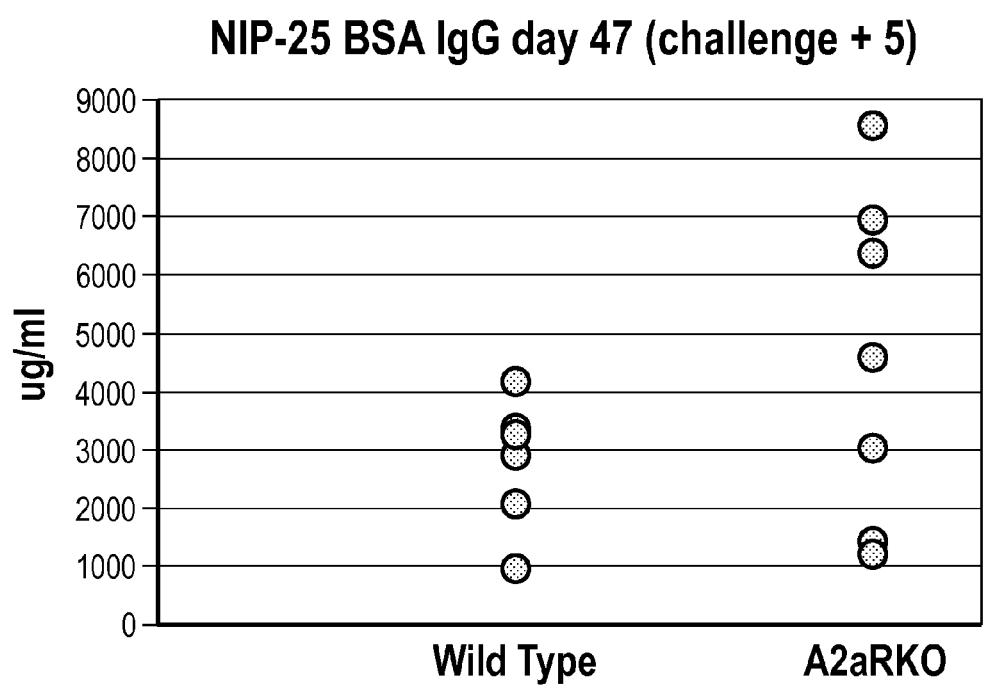
FIG. 11 is a graph showing the amount of NIP-25 BSA IgG in wild type mice and A2a adenosine receptor knockout mice on day 47 (5 day post immune challenge).
Figure 12:
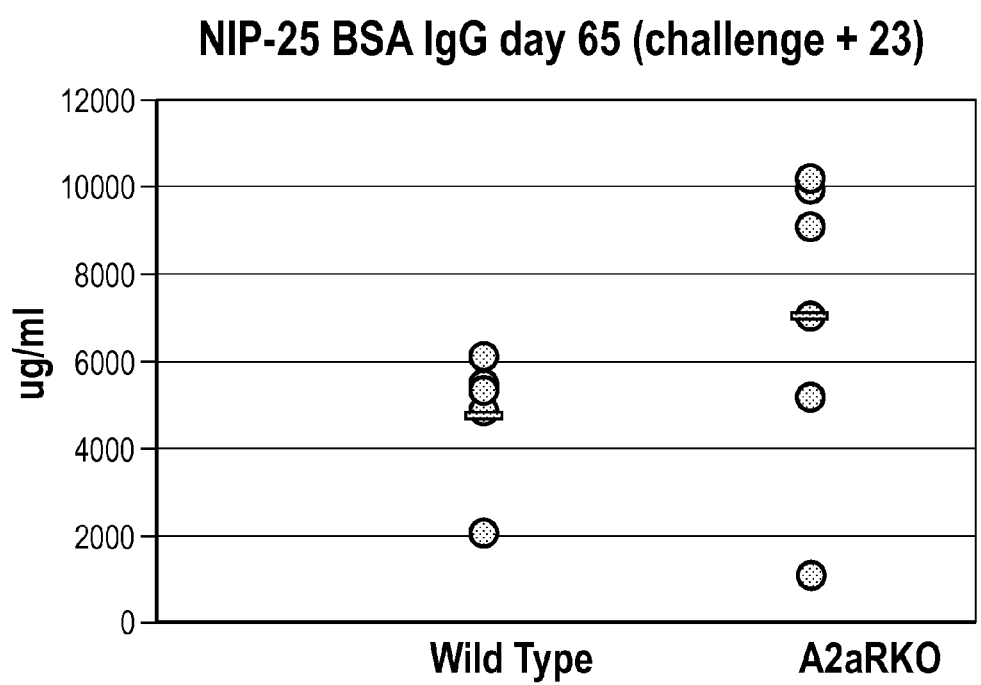
FIG. 12 is a graph showing the amount of NIP-25 BSA IgG in wild type mice and A2a adenosine receptor knockout mice on day 65 (23 day post immune challenge).

Results 5 days and 23 days post immune challenge (i.e., day 47 and day 65 of the assay) showed significant increase in NIP-25 as measured by ELISA in A2a adenosine receptor knockout mice as compare to wild type mice (see FIGS. 11-12). The increased levels of NIP-25 post immune boost and post immune challenge in the A2a adenosine receptor knockout mice indicates an increased titer of antibodies. The increased NIP-25 in A2a adenosine receptor knockout mice shows that in the recall phase of immunization A2a adenosine receptor regulates the expansion of memory B cells. As seen in the A2a adenosine receptor knockout mice, without the A2a adenosine receptor, there is an increase in the NIP-25 (FIGS. 13 and 14) post immune challenge. The results show that antagonizing Gs coupled protein receptor during the later stages of vaccination would be useful in increasing the titer in a vaccine response.

Example 8. Methods for Increasing Antibody Titer after Vaccination

This example will show that treatment with Gs coupled protein antagonists and compounds that inhibit the effects of hypoxia will amplify the antibody titer to vaccination.

Methods and Materials 12 male wild type C57 B/6 mice 10-12 weeks of age are immunized as described in Example 1. At day 21, the mice are given an immune boost of 1 µg NP-OVA with adjuvant via intraperitoneal injection. At day 42, the mice are given an immune challenge of 1 µg NP-OVA without adjuvant via tail vein injection. At day 44 and day 62, six of the mice are given an effective amount of dopamine (Gs coupled protein antagonist) and subject to inspiration of hyperoxic gas mixture (e.g., oxygen concentration greater than the 21% atmospheric concentration of oxygen). Samples at 5 days and 23 days post immune challenge (i.e., day 47 and day 65 of the assay) will be subjected to ELISA measurement for NIP-25.

Results

It is anticipated that mice treated with of dopamine and subject to inspiration of hyperoxic gas mixture will have higher levels of NIP-25 than untreated mice. The increase in NIP-25 in treated mice will show that antagonizing Gs coupled protein receptor and reducing the hypoxic microenvironment of germinal centers during the later stages of vaccination would be useful in increasing the titer in a vaccine response.

Example 9. Methods for Stimulating B Cells Ex Vivo to Improve Class Switching and Overall Activation This example shows that stimulation B cell ex vivo with adenosine receptor agonists improves B cell class switching and activation.

Methods and Materials

C57B/6 mice spleens were harvested and lymphocytes separated by Ficoll. Unseparated lymphocytes were then plated onto 96 well plate and stimulated with anti-IgM Fab2 (Jackson Immunoresearch) at 6 ug/ml, anti-CD40 at 5 ug/ml, and IL-4 20 ng/ml using standard IMDM media. The stimulated cells were incubated in 1% oxygen incubator, which nitrogen was used to keep the oxygen at 1% and 5% $CO_2$. Untreated control cells were incubated a 21% oxygen and 5% $CO_2$. After 3 days of stimulation, class switching was assessed by flow cytometry as described above (cells gated on B220).

Results

Figure 13:
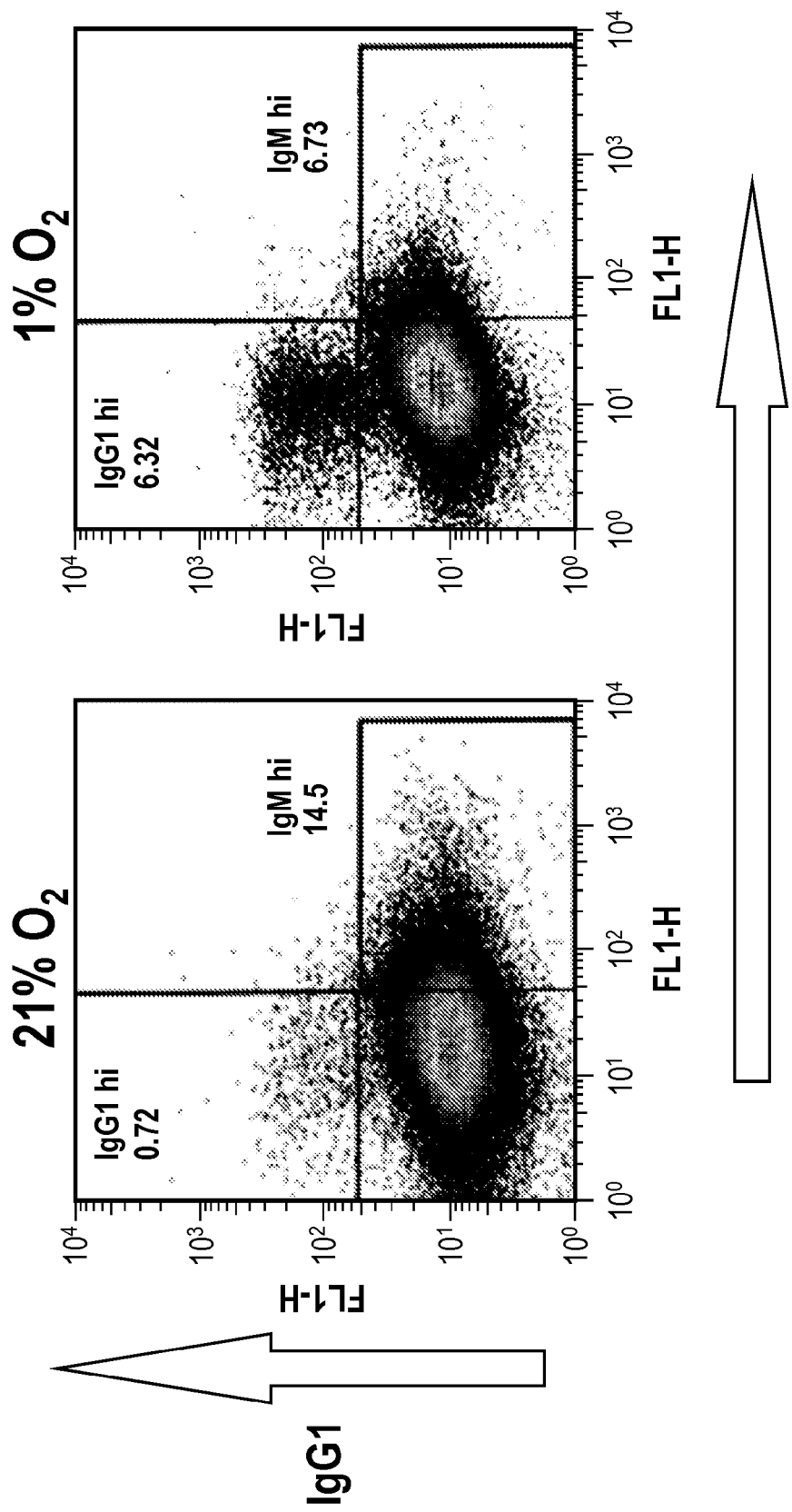
FIG. 13 is are diagram showing that under hypoxic conditions and stimulation with antibodies, CD40 and IgM, and growth factors, IL-4, B cells have improved class switching.

Cell stimulated and grown in 1% oxygen showed an increase in the amount of IgG1 antibody as compared to the untreated (FIG. 13). It is anticipated that treatment with Gs protein coupled receptors, e.g., A2a and/or A2b adenosine receptor agonist will further enhance B cell class switching and activation (see Example 6).

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A method for enhancing an immune response in a subject, comprising:
   administering, after vaccination of the subject, one or more immune enhancers, wherein the immune enhancers are A2a adenosine receptor agonists,
and further comprising administering one or more additional immune enhancers selected from the group consisting of: ibudilast, mesembrine, rolipram, piclamilast, luteolin, drotaverine, and roflumilast.

2. The method of claim 1, wherein enhancing the immune response comprises enhancing the production of high affinity, broadly neutralizing antibodies.

3. The method of claim 1, wherein the A2a adenosine receptor agonist is one or more A2a adenosine receptor agonist selected from the group consisting of:
   CGS21680, ATL146e, YT-146, Regadenozone, and UK42,097.

4. The method of claim 1, wherein one or more of the immune enhancers are administered simultaneously with a vaccine during vaccination.

5. The method of claim 1, wherein the one or more one immune enhancers are administered about 3 to 10 days after vaccination.

6. The method of claim 1, wherein the one or more one immune enhancers are administered daily for about 3 to 42 days after vaccination.

7. The method of claim 1, wherein administration of the immune enhancer increases the nitroiodophenyl (NIP)-5/25 ratio above 0.3.

8. A method for potentiating a germinal center and/or cells within the germinal center in a subject, the method comprising: administering after vaccination of the subject, one or more immune enhancers, wherein the immune enhancers are A2a adenosine receptor agonists,
   and further comprising administering one or more additional immune enhancers selected from the group consisting of: ibudilast, mesembrine, rolipram, piclamilast, luteolin, drotaverine, and roflumilast.

9. The method of claim 8, wherein potentiating the germinal center and/or cells within the germinal center induces the development of high affinity, broadly neutralizing antibodies.

10. The method of claim 8, wherein potentiating the germinal center and/or cells within the germinal center comprises one or more of inducing a hypoxic environment and stimulating A2a and/or A2b adenosine receptors.

11. The method of claim 8, wherein the A2a adenosine receptor agonist is one or more A2a adenosine receptor agonist selected from the group consisting of:
    CGS21680, ATL146e, YT-146, Regadenozone, and UK42,097.

* * * * *

UNITED STATES PATENT AND TRADEMARK OFFICE
CERTIFICATE OF CORRECTION

PATENT NO. : 9,782,428 B2
APPLICATION NO. : 14/777605
DATED : October 10, 2017
INVENTOR(S) : Sitkovsky et al.

Page 1 of 1

It is certified that error appears in the above-identified patent and that said Letters Patent is hereby corrected as shown below:

In the Specification

At Column 1, Line 14, insert:
--GOVERNMENT SUPPORT
This invention was made with government support under Grant Number AI091693 awarded by the National Institutes of Health. The government has certain rights in the invention.--

Signed and Sealed this
Eleventh Day of August, 2020

Andrei Iancu
*Director of the United States Patent and Trademark Office*